United States Patent
Green et al.

(10) Patent No.: US 7,615,229 B2
(45) Date of Patent: Nov. 10, 2009

(54) **MUTANTS OF THE P4 PROTEIN OF NONTYPABLE *HAEMOPHILUS INFLUENZAE* WITH REDUCED ENZYMATIC ACTIVITY**

(75) Inventors: Bruce A. Green, New City, NY (US); Gary W. Zlotnick, New Windsor, NY (US); Leah D. Fletcher, Geneseo, NY (US); Arnold L. Smith, Mercer Island, WA (US); Thomas J. Reilly, Columbia, MO (US)

(73) Assignees: Wyeth Holdings Corporation, Madison, NJ (US); The Curators of the University of Missouri, Columbia, MO (US)

( * ) Notice: Subject to any disclaimer, the term of this patent is extended or adjusted under 35 U.S.C. 154(b) by 777 days.

(21) Appl. No.: 10/507,786

(22) PCT Filed: Mar. 13, 2003

(86) PCT No.: PCT/US03/07895

§ 371 (c)(1),
(2), (4) Date: Sep. 13, 2004

(87) PCT Pub. No.: WO03/078453

PCT Pub. Date: Sep. 25, 2003

(65) Prior Publication Data

US 2005/0249746 A1    Nov. 10, 2005

Related U.S. Application Data

(60) Provisional application No. 60/364,688, filed on Mar. 15, 2002.

(51) Int. Cl.
*A61K 39/02* (2006.01)

(52) U.S. Cl. .............. 424/256.1; 424/282.1; 424/193.1; 424/192.1; 424/185.1; 530/350

(58) Field of Classification Search .............. 424/256.1, 424/282.1, 193.1, 192.1, 185.1; 530/350
See application file for complete search history.

(56) References Cited

U.S. PATENT DOCUMENTS

| | | | |
|---|---|---|---|
| 4,518,526 A | 5/1985 | Olson |
| 4,542,104 A | 9/1985 | Stryer et al. |
| 4,554,101 A | 11/1985 | Hopp |
| 4,599,197 A | 7/1986 | Wetzel |
| 4,734,362 A | 3/1988 | Hung et al. |
| 4,777,127 A | 10/1988 | Suni et al. |
| 4,912,094 A | 3/1990 | Myers et al. |
| 5,057,540 A | 10/1991 | Kensil et al. |
| 5,078,996 A | 1/1992 | Conlon, III et al. |
| 5,091,309 A | 2/1992 | Schlesinger et al. |
| 5,185,440 A | 2/1993 | Davis et al. |
| 5,217,879 A | 6/1993 | Huang et al. |
| 5,219,740 A | 6/1993 | Miller et al. |
| 5,272,257 A | 12/1993 | Gupta |
| 5,580,859 A | 12/1996 | Felgner et al. |
| 5,593,972 A | 1/1997 | Weiner et al. |
| 5,601,831 A | 2/1997 | Green et al. |
| 5,698,202 A | 12/1997 | Ertl et al. |
| 5,703,055 A | 12/1997 | Felgner et al. |
| 5,723,127 A | 3/1998 | Scott et al. |
| 5,739,118 A | 4/1998 | Carrano et al. |
| 5,780,601 A | 7/1998 | Green et al. |
| 5,837,533 A | 11/1998 | Boutin |
| 5,955,580 A | 9/1999 | Green et al. |
| 6,083,716 A | 7/2000 | Wilson et al. |
| 6,113,918 A | 9/2000 | Johnson et al. |
| 6,127,170 A | 10/2000 | Boutin |
| 6,168,918 B1 | 1/2001 | Satishchandran et al. |
| 6,207,646 B1 | 3/2001 | Krieg et al. |

FOREIGN PATENT DOCUMENTS

| | | |
|---|---|---|
| EP | 345242 | 12/1989 |
| EP | 415731 | 3/1991 |
| EP | 462210 | 12/1991 |
| EP | 606921 | 7/1994 |
| GB | 2200651 | 8/1988 |
| WO | WO-90/07936 | 7/1990 |
| WO | WO-91/02805 | 3/1991 |
| WO | WO-90/10458 | 12/1991 |
| WO | WO-92/10578 | 6/1992 |
| WO | WO-92/19265 | 11/1992 |
| WO | WO-93/03769 | 3/1993 |
| WO | WO-93/09239 | 5/1993 |
| WO | WO-93/10218 | 5/1993 |
| WO | WO-93/11230 | 6/1993 |
| WO | WO-93/13202 | 7/1993 |
| WO | WO-93/19191 | 9/1993 |
| WO | WO-93/25234 | 12/1993 |
| WO | WO-93/25698 | 12/1993 |
| WO | WO-94/03622 | 2/1994 |
| WO | WO-94/12649 | 6/1994 |
| WO | WO-94/16737 | 8/1994 |
| WO | WO-94/21792 | 9/1994 |
| WO | WO-94/28938 | 12/1994 |
| WO | WO-95/00655 | 1/1995 |

(Continued)

OTHER PUBLICATIONS

Mikayama et al. (Nov. 1993. Proc.Natl.Acad.Sci. USA, vol. 90 : 10056-10060.*

(Continued)

*Primary Examiner*—Jennifer E Graser
(74) *Attorney, Agent, or Firm*—Alan M. Gordon; Howson & Howson LLP

(57) ABSTRACT

A P4 variant protein that has reduced enzymatic activity and that induces antibody to wild-type P4 protein and/or has good bactericidal activity against non-typable *H. influenzae* (NTHi) is useful as an active component in an immunogenic composition for humans. Methods of using these proteins, and compositions containing them in combination with additional antigens, are also provided.

34 Claims, No Drawings

FOREIGN PATENT DOCUMENTS

| | | |
|---|---|---|
| WO | WO-95/07994 | 3/1995 |
| WO | WO-95/11984 | 5/1995 |
| WO | WO-95/27044 | 10/1995 |
| WO | WO-95/27069 | 10/1995 |
| WO | WO-96/10038 | 4/1996 |
| WO | WO-99/21591 | 5/1999 |
| WO | WO-99/45966 | 9/1999 |
| WO | WO-00/18434 | 4/2000 |
| WO | WO-00/28061 | 5/2000 |
| WO | WO-00/55335 | 9/2000 |
| WO | WO-01/83692 | 11/2001 |

OTHER PUBLICATIONS

Rudinger et al. (Jun. 1976. Peptide Hormones. Biol.Council. pp. 5-7.*

Gase et al., "The IppC gene of *Streptococcus equisimilis* encodes a lipoprotein that is homologous to the e (P4) outer membrane protein from *Haemophilus influenzae*", *Med. Microbiol. Immunol.* Jun. 1997 186(1):63-73.

Green et al., "Certain site-directed, nonenzymatically active mutants of the *Haemophilus influenzae* P4 lipoprotein are able to elicit bactericidal antibodies", *Infec. & Immun.* Jul. 2005 73(7): 4454-4457.

Communication—Supplementary European Search Report in European Application No. EP 03714153, mailed May 24, 2006.

Alvarado-Urbina et al., "Automated synthesis of gene fragments", *Science* Oct. 16, 1981 214:270-274.

Amann et al., "Tightly regulated tac promoter vectors useful for the expression of unfused and fused proteins in *Escherichia coli*", *Gene* Sep. 30, 1988 69(2):301-315.

Andersen et al., "Herpesvirus-mediated gene delivery into the rat brain: specificity and efficiency of the neuron-specific enolase promoter", *Cell. Mol. Neurobiol.* Oct. 1993 13(5):503-515.

Arbuthnot et al., "In vitro and in vivo hepatoma cell-specific expression of a gene transferred with an adenoviral vector", *Human Gene Ther.* Aug. 20, 1996 7(13):1503-1514.

Barba et al., "Thymidine kinase-mediated killing of rat brain tumors", *J. Neurosurg.* Nov. 1993 79(5):729-735.

Berkner, K.L., "Development of adenovirus vectors for the expression of heterologous genes", *Biotech.* Jul.-Aug. 1988 6(7):616-629.

Boshart et al., "A very strong enhancer is located upstream of an immediate early gene of human cytomegalovirus", *Cell* Jun. 1985 41(2):521-530.

Caillaud et al., "Adenoviral vector as a gene delivery system into cultured rat neuronal and glial cells", *Eur. J. Nuerosci.* Oct. 1, 1993 5(10):1287-1291.

Chen et al., "Expression of rat bone sialoprotein promoter in transgenic mice", *J. Bone Miner Res.* May 1996 11(5):654-664.

Collins et al., "Molecular sequence comparison and alignment" in Practical Approach Series: Nucleic Acid and Protein Sequence Analysis XVIII, (M.J. Bishop et al., eds.) IRL Press: Oxford, England, UK 1987 pp. 417.

Collins et al., "The significance of protein sequence similarities", *Comput. Appl. Biosci.* Mar. 1988 4(1):67-71.

Deich et al., "Cloning of genes encoding a 15,000-dalton peptidoglycan-associated outer membrane lipoprotein and an antigenically related 15,000-dalton protein from *Haemophilus influenzae*", *J. Bacteriol.* Feb. 1988 170(2):489-498.

Fleischmann et al., "Whole-genome random sequencing and assembly of *Haemophilus influenzae* Rd", *Science* Jul. 28, 1995 269(5223):496-512.

Flotte et al., "Stable in vivo expression of the cystic fibrosis transmembrane conductance regulator with an adeno-associated virus vector", *Proc. Natl. Acad. Sci. USA* Nov. 15, 1993 90(22):10613-10617.

Gething et al., "Cell-surface expression of influenza haemagglutinin from a cloned DNA copy of the RNA gene", *Nature* Oct. 22, 1981 293(5834):620-625.

Gossen et al., "Tight control of gene expression in mammalian cells by tetracycline-responsive promoters", *Proc. Natl. Acad. Sci. USA* Jun. 15, 1992 (12):5547-5551.

Gossen et al., "Transcriptional activation by tetracyclines in mammalian cells", *Science* Jun. 23, 1995 268(218):1766-1769.

Green et al., "A recombinant non-fatty acylated form of the Hi-PAL (P6) protein of *Haemophilus influenzae* elicits biologically active antibody against both nontypeable and type b *H. influenzae*", *Infect. Immun.* Oct. 1990 58(10):72-3278.

Green et al., "The e(P4) outer membrane protein of *Haemophilus influenzae*: Biologic activity of anti-e serum and cloning and sequencing of the structural gene", *Infect. And Immun.* Sep. 1991 59(9):3191-3198.

Guzman et al., "Efficient and selective adenovirus-mediated gene transfer into vascular neointima", *Circulation* Dec. 1993 88(6):2838-2848.

Guzman et al., "Efficient gene transfer into myocardium by direct injection of adenovirus vectors", *Circulation* Dec. 1993 73(6):1202-1207.

Guzman et al., "Tight regulation, modulation, and high-level expression by vectors containing the arabinose PBAD promoter", *J. Bacteriol.* Jul. 1995 177(14):121-4130.

Hansal et al., "Induction of antigen-specific hyporesponsiveness by transplantation of hemopoietic cells containing an MHC class I transgene regulated by a lymphocyte-specific promoter", *J. Immunol.* Aug. 1, 1998 161(3):063-1068.

Harvey et al., "Inducible control of gene expression: prospects for gene therapy", *Curr. Opin. Chem. Biol.* Aug. 1998 2(4):512-518.

Henry, "Gene therapy", *Chem. Eng. News* Nov. 26, 2001 79(48):35-41.

Jaffe et al., "Adenovirus-mediated in vivo gene transfer and expression in normal rat liver", *Nat. Genet.* Aug. 1992 1(5):372-378.

Kass-Eisler et al., "Quantitative determination of adenovirus-mediated gene delivery to rat cardiac myocytes in vitro and in vivo", *Proc. Natl. Acad. Sci. USA* Dec. 15, 1993 90(24):11498-11502.

Kemmer et al., "NadN and e(P4) are essential for utilization of NAD and Nicotinamide mononucleotide but not Nicotinamide riboside in *Haemophilus influenzae*", *J. of Bacteriol.* Jul. 2001 183(13):3974-3981.

Kolls et al., "Prolonged and effective blockade of tumor necrosis factor activity through adenovirus-mediated gene transfer", *Proc. Natl. Acad. Sci. USA* Jan. 4, 1994 91(1):215-219.

Levrero et al., "Defective and nondefective adenovirus vectors for expressing foreign genes in vitro and in vivo", *Gene* May 30, 1991 101(2):195-202.

Li et al., "Assessment of recombinant adenoviral vectors for hepatic gene therapy", *Human Gene Ther.* Aug. 1993 4(4):403-409.

Li et al., "Synthetic muscle promoters: activities exceeding naturally occurring regulatory sequences", *Nat. Biotech.* Mar. 1999 17(3):241-245.

Magari et al., "Pharmacologic control of a humanized gene therapy system implanted into nude mice", *J. Clin. Invest.* Dec. 1, 1997 100(11):2865-2872.

Matteucci et al., "Synthesis of deoxyoligonucleotides on a polymer support", *J. Am. Chem. Soc.* 1981 103(11):3185-3191.

Mendelson et al., "Expression and rescue of a nonselected marker from an integrated AAV vector", *Virol.* Sep. 1988 166(1):154-165.

Merrifield, "Solid phase peptide synthesis. I. The synthesis of a tetrapeptide", *J. Am. Chem. Soc.* Jul. 20, 1963 85:2149-2154.

Miyatake et al., "Transcriptional targeting of herpes simplex virus for cell-specific replication", *J. Virol.* Jul. 1997 71(7):5124-5132.

No et al., "Ecdysone-inducible gene expression in mammalian cells and transgenic mice", *Proc. Natl. Acad. Sci. USA* Apr. 16, 1996 93(8):3346-3351.

Piccioli et al., "Neuroantibodies: ectopic expression of a recombinant anti-substance P antibody in the central nervous system of transgenic mice", *Neuron* Aug. 1995 15(2):373-384.

Piccioli et al., "Neuroantibodies: molecular cloning of a monoclonal antibody against substance P for expression in the central nervous system", *Proc. Natl. Acad. Sci. USA* Jul. 1, 1991 88(13):5611-5615.

Ram et al., "In situ retroviral-mediated gene transfer for the treatment of brain tumors in rats", *Cancer Res.* Jan. 1, 1993 53(1):83-88.

Rattan et al., "Protein synthesis, posttranslational modifications, and aging", *Ann. N.Y. Acad. Sci.* Nov. 21, 1992 663:48-62.

Reidl et al., "Lipoprotein e(P4) is essential for hemin uptake by *Haemophilus influenzae*", *J. Exp. Med.* Feb. 1996 183:621-629.

Reidl et al., "NADP and NAD utilization in *Haemophilus influenzae*", *Mol. Microbiol.* Mar. 2000 35(6):1573-1581.

Reilly et al., "Contibution of the DDDD motif of *H. influenzae* e(P4) to phosphomonoesterase activity and heme transport", *FEBS Lett.* Apr. 6, 2001 494(1-2):19-23.

Reilly et al., "Outer membrane lipoprotein e(P4) of *Haemophilus influenzae* is a novel phosphomonoesterase", *J. of Bacteriol.* Nov. 1999 181(21):6797-6805.

Reilly et al., "Purification and characterization of a recombinant *Haemophilus influenzae* outer membrane phosphomonoesterase e (P4)", *Prot. Exp. Purif.* Dec. 1999 17(3):401-409.

Rosenfeld et al., "Adenovirus-mediated transfer of a recombinant alpha 1-antitrypsin gene to the lung epithelium in vivo", *Science* Apr. 19, 1991 252(5004):431-434.

Samulski et al., "Helper-free stocks of recombinant adeno-associated viruses: normal integration does not require viral gene expression", *J. Virol.* Sep. 1989 63(9):3822-3828.

Sandig et al., "HBV-derived promoters direct liver-specific expression of an adenovirally transduced LDL receptor gene", *Gene Ther.* Nov. 1996 3(11):1002-1009.

Seifter et al., "Analysis for protein modifications and nonprotein cofactors", *Meth. Enzymol.* 1990 182:626-646.

Shpaer et al., "Sensitivity and selectivity in protein similarity searches: a comparison of Smith-Waterman in hardware to BLAST and FASTA", *Genomics* Dec. 1, 1996 38(2):179-191.

Sinha et al., "Polymer support oligonucleotide synthesis XVIII: use of β-cyanoethyl-N,N-dialkylamino-/N-morpholino phosphoramidite of deoxynucleodies for the synthesis of DNA fragments simplifying deprotection and isolation of the final product", *Nucl. Acids* 1984 12(11):4539-4557.

Stein et al., "The osteocalcin gene: a model for multiple parameters of skeletal-specific transcriptional control", *Mol. Biol.* Aug. 1997 24(3):185-196.

Stemmer et al., "Single-step assembly of a gene and entire plasmid from large numbers of oligodeoxyribonucleotides", *Gene* Oct. 16, 1995 164(1):49-53.

Studier et al., "Use of T7 RNA polymerase to direct expression of cloned genes", *Meth. Enzymol.* 1990 185:60-89.

Takamiya et al., "Gene therapy of malignant brain tumors: a rat glioma line bearing the herpes simplex virus type 1-thymidine kinase gene and wild type retrovirus kills other tumor cells", *J. Neurosci.* Nov. 1992 33(3):493-503.

Thaller et al., "Conserved sequence motifs among bacterial, eukaryotic, and archaeal phosphatases that define a new phosphohydrolase superfamily", *Protein Sci.* Jul. 1998 7(7):1647-1652.

Vile et al., "In vitro and in vivo targeting of gene expression to melanoma cells", *Cancer Res.* Mar. 1, 1993 53(5):962-967.

Vile et al., "Use of tissue-specific expression of the herpes simplex virus thymidine kinase gene to inhibit growth of established murine melanomas following direct intratumoral injection of DNA", *Cancer Res.* Sep. 1, 1993 53(17):3860-3864.

Vincent et al., "Long-term correction of mouse dystrophic degeneration by adenovirus-mediated transfer of a minidystrophin gene", *Nat. Genet.* Oct. 1993 5(2):130-134.

Wang et al., "Ligand-inducible and liver-specific target gene expression in transgenic mice.", *Nat. Biotech.* Mar. 1997 15(3):239-243.

Wang et al., "Positive and negative regulation of gene expression in eukaryotic cells with an inducible transcriptional regulator", *Gene Ther.* May 1997 4(5):432-441.

Wold, F., "Posttranslational protein modifications: Perspectives and prospects", in Posttranslational Covalent Modification of Proteins, B.C., Johnson, Ed., Academic Press, New York 1983 pp. 1-12.

Zabner et al., "Adenovirus-mediated gene transfer transiently corrects the chloride transport defect in nasal epithelia of patients with cystic fibrosis", *Cell* Oct. 22, 1993 75(2):207-216.

NCBI Accession No. M68502, Oct. 28, 1994.

\* cited by examiner

MUTANTS OF THE P4 PROTEIN OF NONTYPABLE *HAEMOPHILUS INFLUENZAE* WITH REDUCED ENZYMATIC ACTIVITY

CROSS-REFERENCE TO RELATED APPLICATIONS

This application is a national phase of International Patent Application No. PCT/US03/07895, filed Mar. 13, 2003, which claims the benefit of the priority of U.S. Provisional Patent Application No. 60/364,688, filed Mar. 15, 2002.

STATEMENT REGARDING FEDERALLY SPONSORED RESEARCH OR DEVELOPMENT

This invention was supported in part by funds from the United States government (National Institutes of Health, Department of Health and Human Services, Grant No. DHHS-5-R01-A144002-02). The United States government may therefore have certain rights in this invention.

FIELD OF THE INVENTION

This invention relates generally to the fields of immunogenic compositions, and more particularly, immunogenic compositions against otitis media.

BACKGROUND OF THE INVENTION

Non-typable *Haemophilus influenzae* (NTHi) causes diseases in humans including pneumonia, otitis media, sinusitis, and acute febrile tracheobronchitis in adults. This bacterium is also a frequent etiologic agent of otitis media in children and infants. Because infection with NTHi confers only strain-specific immunity, humans can be repeatedly infected. In fact, the most chronic disease caused by this bacterium is repeat otitis in children, resulting in treatments including repetitive exposure to antibiotics or surgery to insert drainage tubes in the ear.

None of the immunogenic compositions available to treat typable *H. influenzae* strains (which are characterized by a known capsule) are useful in the treatment of NTHi. Thus, considerable research has been conducted to find a component that would be useful in preventing infection caused by NTHi. In investigations of candidate components to prevent the occurrence of otitis media in humans, the bacterial lipoprotein called Protein 4 (P4; previously referred to as "outer membrane protein e") of NTHi has been identified as a desirable component because of its ability to elicit bactericidal antibodies to the bacterium in humans. P4 has been found to elicit bactericidal antibodies, which act in synergy with antibodies against other outer membrane proteins of NTHi. Because of this, the protein may be used in conjunction with other outer membrane proteins to induce a more potent bactericidal response.

The hel gene that encodes P4 is antigenically conserved within and between strains of *H. influenzae*. See, e.g., U.S. Pat. Nos. 5,780,601; 5,955,580 and 5,601,831 and European Patent Nos. EP 0 606 921 and EP 0 462 210, among others, which are hereby incorporated by reference. The sequences of the hel gene (SEQ ID NO: 1) and the encoded, 274 amino acid, pre-protein (SEQ ID NO: 2) are available from the NCBI database, Accession No. M68502 and identified in Green, B. A., et al, 1991 Infect. Immun., 59(9):3191-3198. The mature P4 of NTHi is a lipidated protein of 254 amino acids in length (SEQ ID NO: 3), encoded by nucleotides 209-970 of SEQ ID NO: 1. The 274 amino acid unprocessed pre-P4 protein has a 20 amino acid signal peptide that specifies a site for fatty acid acylation (SEQ ID NO: 2, amino acids 1-20), and is encoded by nucleotides 149-970 of SEQ ID NO: 1, with nucleotides 149-208 encoding the signal or leader peptide.

The function of the P4 protein in *Haemophilus* was originally thought to be hemin transport (Reidl, J., and J. J. Mekalanos. 1996 J. Exp. Med., 183:621-629.5). However, the P4 protein was later discovered to be an outer membrane enzyme, i.e., a bacterial acid phosphatase (Reilly, T. J. et al, 1999 J. Bacteriol., 181:6797-805). More recent work in the area has shown differing opinions by laboratories as to the true function of the P4 protein (Kemmer, G. et al, 2001 J. Bacteriol., 183:3974-3981; Reidl, J. et al, 2000 Mol. Microbiol., 35:1573-81; Reilly, T., and A. Smith, 1999 Prot. Exp. Purif., 17:401-409; Reilly, T. J. et al, 1999. J. Bacteriol., 181:6797-805; and Reilly, T. J. et al, 2001 FEBS Lett., 494: 19-23).

The identification of P4 as an enzymatic protein has created a potential concern for its use as a component of an immunogenic composition for humans. This protein is enzymatically active and its in vivo substrate is not completely defined. While wild-type P4 has no known detrimental effects when administered into humans, it is generally accepted that non-enzymatically active proteins or those with reduced activity are preferred to enzymatically active proteins for use in immunogenic compositions to be administered to humans. An enzymatically active protein is not preferred for use as an immunogenic component because its enzymatic activity may cause an unexpected, undesired, reaction in the immunized human, other than the induction of antibodies.

Fragments of P4 protein or variant "mutant" P4 sequences described generally by the above-mentioned documents and patents are not characterized in terms of the most important property for an immunogenic composition, i.e. immunogenicity. No information is provided on the effects of mutation on immunogenicity. Further no indications are provided that changes that effect enzymatic activity have any effect on immunogenic potential. Thus, nothing in the prior art provides any direction for the selection of mutants of the P4 protein to yield a component for an immunogenic composition.

A continuing need exists in the art for therapeutic and prophylactic compositions comprising NTHi P4 variant proteins, which have reduced enzymatic activity and which are immunologically equivalent to the wild-type protein, for safe use in immunogenic compositions in humans.

SUMMARY OF THE INVENTION

In one aspect, the invention provides a P4 variant (mutant) protein that has reduced enzymatic activity compared to wild-type P4 protein and that induces antibody to wild-type P4 protein and/or that has bactericidal activity against NTHi. This variant protein is useful in inducing a protective immune response against NTHi in an immunized human.

In another aspect, the invention provides an immunogenic composition comprising an NTHi P4 variant protein as described herein, a pharmaceutically acceptable carrier and, optionally, an adjuvant. This composition may contain additional antigenic proteins or peptides and is useful in inducing a protective immune response against NTHi.

In yet a further aspect, the invention provides isolated or recombinant nucleotide molecules comprising a nucleic acid sequence encoding a P4 variant of the invention. The invention also entails vectors such as plasmids, recombinant viruses, etc., containing these molecules under regulatory control of sequences directing the expression of the variant in a host cell.

Still another aspect of this invention provides a host cell comprising a vector containing a nucleotide molecule as described herein.

Yet another aspect of this invention includes methods for inducing an immune response in a human against NTHi by administering the variant protein or compositions containing it.

A still further aspect of the invention involves methods for the recombinant expression of a P4 variant protein by a host cell transformed, transfected or transduced with a vector containing these molecules.

Another aspect of this invention includes the use of a P4 variant protein as a carrier for another antigen, where the other antigen may be a protein, polypeptide, peptide, polysaccharide, oligosaccharide, saccharide, lipopolysaccharide, lipooligosaccharide, or liposaccharide. The variant P4 protein has reduced enzymatic activity compared to wild-type P4 protein, but need not necessarily either induce antibody to wild-type P4 protein or have bactericidal activity against NTHi, with the proviso that the P4 variant carrier protein does not have a phenylalanine at amino acid position 122 of SEQ ID NO:3.

These and other aspects of the invention will be apparent to one of skill in the art upon reading of the following detailed description of the invention.

DETAILED DESCRIPTION OF THE INVENTION

The present invention meets the needs of the art by providing a non-enzymatically-active P4 variant protein that induces antibody to wild-type P4 protein and/or has bactericidal activity against NTHi. Compositions containing such P4 variant proteins, nucleic acid molecules encoding them, and methods of use of such proteins and nucleic acid molecules provide novel means for inducing immunity to NTHi in humans.

A. Variant P4 Proteins of this Invention

Variant P4 proteins are defined as mutant P4 proteins that have either very low levels of P4 enzyme activity, or no detectable P4 enzymatic activity. When used as components in immunogenic compositions, these variant P4 proteins retain desirable immunologic properties of the wild-type P4 protein. These properties include elicitation of ELISA reactive antibodies against wild-type P4 and/or bactericidal antibodies against NTHi. When used as carrier proteins, the variant P4 proteins need not retain the immunologic properties of the wild-type P4 protein.

Because the clinical correlate of protection against NTHi is not known, substituting a mutant P4 for wild-type P4 in an immunogenic composition can only be successful if the mutant elicits ELISA titers and/or bactericidal titers equivalent to those elicited by wild-type recombinant lipoprotein P4 (rLP4). Such variant P4 proteins are desirable components of immunogenic compositions useful for prophylaxis of NTHi infection. As used herein, the terms "variant P4 protein" or "mutant P4 protein" refer to a protein or lipoprotein bearing specific mutations at amino acid residues that substantially ablate the wild-type P4 enzymatic activity, and yet permit retention of the protein's ability to induce an immune response to NTHi in a human.

By "immune response" or "immunity" as the terms are interchangeably used herein, is meant the induction of a humoral (i.e., B cell) and/or cellular (i.e., T cell) response.

Suitably, a humoral immune response may be assessed by measuring the P4 antigen-specific antibodies present in serum of immunized animals in response to introduction of the P4 protein variants of this invention into a host. In one exemplary embodiment below, the immune response is assessed by the enzyme linked immunosorbant assay (ELISA) of sera of immunized animals. A cytotoxic T lymphocyte (CTL) assay can be employed to measure the T cell response from lymphocytes isolated from the spleen of immunized animals.

Preferably the variant P4 protein of this invention is a lipoprotein, i.e., it contains a modified cysteine at its amino-terminus, to which a fatty acylated glycerol is thioether-linked and a fatty acid is linked to its terminal amino group. In one embodiment of a P4 variant protein of this invention, the leader peptide is the wild-type P4 leader peptide of $H.$ $influenzae$, i.e., amino acids 1 to 20 of SEQ ID NO: 2. However, other peptides specifying a site for fatty acylation in a bacterial cell may be fused to the P4 variant protein in place of the wild-type sequence to provide a lipoprotein. Examples of other leader peptides include those from the P6 protein of $H.$ $influenzae$, the OspA protein of $Borrelia$ $burgdorferi$ and those from gram-positive bacterial lipid signal peptides.

In yet another embodiment of this invention, where the P4 variant protein is used as a carrier protein, it may preferably be non-lipidated, i.e., it is expressed without a leader peptide. For example, it lacks the leader peptide of amino acids 1-20 of SEQ ID NO: 2 or it is fused to a leader peptide that lacks a site for fatty acylation.

Throughout this specification, the identification of the amino acid residue at which the specific mutations are located is that residue number corresponding to the processed, mature lipidated amino acid sequence of wild-type P4, i.e., SEQ ID NO: 3.

This invention is directed to a P4 variant protein of NTHi that has reduced enzymatic activity compared to wild-type P4 protein and that induces antibody to wild-type P4 protein and/or that has bactericidal activity against NTHi, wherein the P4 variant protein has a mutation selected from the group consisting of:

(a) a mutation at amino acid residue 39 of SEQ ID NO: 3, which is a glutamine in wild-type P4 protein;

(b) a mutation at amino acid residue 48 of SEQ ID NO: 3, which is a phenylalanine in wild-type P4 protein;

(c) a mutation at amino acid residue 64 of SEQ ID NO: 3, which is an aspartic acid in wild-type P4 protein;

(d) a mutation at amino acid residue 161 of SEQ ID NO: 3, which is a lysine in wild-type P4 protein;

(e) a mutation at amino acid residue 218 of SEQ ID NO: 3, which is an asparagine in wild-type P4 protein;

(f) mutations at amino acid residues 35 and 37 of SEQ ID NO: 3, which are alanine in wild-type P4 protein, where the mutations are not glutamic acid, glutamine or threonine;

(g) mutations at amino acid residues 64 and 66 of SEQ ID NO:3, which are aspartic acid in wild-type P4 protein; and (h) combinations of one or more of the mutations of (a)-(g).

Specifically, a first embodiment of a specific P4 variant protein of this invention is a protein that contains a mutation at amino acid residue 39 of SEQ ID NO: 3, which is a glutamine in wild-type P4 protein. In one embodiment, the P4 variant protein contains a glutamic acid at amino acid position 39 of SEQ ID NO: 3. Alternatively, the P4 variant protein contains an aspartic acid or asparagine at amino acid position 39 of SEQ ID NO:3.

A second embodiment of a P4 variant protein of this invention contains a mutation at amino acid residue number 48, which is a phenylalanine in wild-type P4 protein. Desirably, that amino acid residue in the P4 variant protein is a cysteine. The substitution of a Cys residue for the Phe residue at position 48 is a non-conservative change that might have been expected to disrupt protein structure. However, this P4 variant protein has desirable antigenic and immunogenic properties. This P4 variant protein also lacks the ability to complement hemA mutations in *E. coli*. See, Reilly, T. J. et al, 2001 FEBS Lett. 494:19-23, incorporated herein by reference in its entirety. Alternatively, the P4 variant protein contains a serine or other amino acids which have uncharged polar groups, such as glycine, threonine, tyrosine, asparagine and glutamine, at amino acid position 48 of SEQ ID NO: 3.

A third embodiment of a P4 variant protein of this invention contains a mutation at amino acid residue position 64 of SEQ ID NO:3, which is aspartic acid in wild-type P4 protein. In one embodiment, the P4 variant protein contains an asparagine or glutamic acid at residue 64. Alternatively, the P4 variant protein contains alanine at amino acid position 64 of SEQ ID NO: 3.

A fourth embodiment of a P4 variant protein of this invention contains a mutation at amino acid residue position 161 of SEQ ID NO: 3, which is lysine in wild-type P4 protein. In one embodiment, the P4 variant protein contains an arginine at residue 161.

A fifth embodiment of a P4 variant protein of this invention contains a mutation at amino acid residue position 218 of SEQ ID NO: 3, which is asparagine in wild-type P4 protein. In one embodiment, the P4 variant protein contains a glutamine at residue 218. Alternatively, the P4 variant protein contains an aspartic acid or glutamic acid at amino acid position 218 of SEQ ID NO: 3.

A sixth embodiment of a P4 variant protein of this invention contains mutations at amino acid residue positions 35 and 37 of SEQ ID NO: 3, which are alanine in wild-type P4 protein. In one embodiment, the P4 variant protein contains an asparagine at residues 35 and 37. The P4 variant protein does not contain an glutamic acid, glutamine or threonine at amino acid positions 35 and 37 of SEQ ID NO: 3.

A seventh embodiment of a P4 variant protein of this invention contains mutations at amino acid residue positions 64 and 66 of SEQ ID NO: 3, which are aspartic acid in wild-type P4 protein. In one embodiment, the P4 variant protein contains an alanine at residues 64 and 66. Alternatively, the P4 variant protein contains asparagine or glutamic acid at amino acid positions 64 and 66 of SEQ ID NO: 3.

The inventors determined that elimination or reduction of enzymatic activity in P4 variant proteins follows no obvious pattern as to whether immunogenicity against wild-type P4 is preserved. Several mutations in the P4 sequence eliminate or reduce enzymatic activity, but also render the mutant proteins incapable of eliciting either high ELISA titers or high bactericidal titers. The inventors observed a lack of correlation between enzymatic activity and immunogenicity, between high ELISA titers and high bactericidal titers and between predictability of effects of conserved changes on antigenic structure in a variety of P4 variant proteins that were investigated and identified below in the examples.

For example, initial attempts to eliminate enzymatic activity in P4 protein were made at the known DD motifs (two adjacent or nearby aspartic acid residues) common to bacterial acid phosphatases (Thaller, M. C. et al, 1998. Prot. Sci., 7:1647-52), i.e., amino acid residues 64 and 66 of SEQ ID NO: 3 and amino acid positions 184 and 185 of SEQ ID NO:3. When P4 variant proteins containing either a double mutant of two alanines in place of the two aspartic acids at positions 64 and 66 or a double mutant of two alanines in place of the two aspartic acids at positions 184 and 185 were evaluated for enzymatic activity, both were enzymatically inactive.

However, when these proteins were used to immunize mice, the antisera produced showed low ELISA titers against wild-type P4. This was shown to be due to a change in epitopes recognized by the antibodies, as the antisera had high titers against the homologous proteins. In contrast, when the bactericidal activity of these antisera was evaluated, antisera to both mutant proteins showed high levels of bactericidal activity for the D64A, D66A mutant and low levels of bactericidal activity for the D184A, D185A mutant. Thus, the D64A, D66A mutant is a useful component for inclusion in an immunogenic composition, while the D184, D185A mutant is not. Another proposed mutant contained a substitution of the Asp residue at position 64 with a highly conservative Glu residue, resulting in a P4 variant (D64E) that elicited high ELISA titers against wild-type P4, even though it had low bactericidal titers against NTHi. Still other proposed mutant P4 proteins that do not satisfy the criteria for P4 variant proteins useful as components of an immunogenic composition of this invention are shown in the examples below.

Other useful P4 variant proteins useful in this invention include a full-length mature 254 amino acid lipoprotein with one or more of the specific mutations provided above, or a polypeptide or a fragment thereof containing the mutagenized residues described above and which protein, polypeptide or fragment retains the reduced enzymatic activity, ELISA and/or bactericidal (BC) activities of the full-length P4 variant from which it is derived.

Immunologically active, enzymatically inactive fragments of these P4 variant proteins ordinarily will contain at least at least about 25 contiguous amino acids of the P4 variant proteins containing the site of mutagenesis noted above. More typically a P4 variant protein fragment contains at least about 100 contiguous amino acids. Another fragment of a P4 variant protein contains at least about 150 contiguous amino acids. Still another embodiment of a P4 variant protein contains at least about 200 contiguous amino acids in length.

A fragment of the P4 variant protein is useful in the methods described below if it induces a protective immune response to NTHi in the subject. Fragments include truncations of the carboxy-terminal region of the P4 protein. For example, a P4 variant protein truncated at about residue 200 (that is, it contains amino acids 1-200 of SEQ ID NO:3) is a desirable fragment. Similarly, P4 variant proteins truncated at about residues 210, 221 or 232 are desirable fragments. Still other fragments of the non-enzymatically active, immunologically active P4 variants of this invention may be selected. The foregoing fragments may also contain one or more of the specific mutations described above.

Other suitable P4 variant proteins may include those in which one or more of the amino acid residues includes a substituted group. Still another suitable P4 variant protein is one in which the polypeptide is fused with another compound, such as a compound to increase the half-life of the polypeptide (for example, polyethylene glycol). Another suitable P4 variant protein is one in which additional amino acids are fused to the polypeptide, such as a leader or secretory sequence, or a sequence which is employed to enhance the immunogenicity of the P4 variant protein. Still other modifications of the P4 variant protein include the above-mentioned deletion of the signal or leader sequence at the N terminus of P4, i.e., encoded by nucleotides 148-208 of SEQ ID NO: 1 and/or the deletion of other regions that do not effect immunogenicity. Similarly, a modification of the P4 variant proteins described herein includes include replacing the signal or leader sequence with another signal or leader sequence. See, e.g., U.S. Pat. No. 5,780,601, incorporated by reference herein.

Still another example of suitable P4 variant proteins are those in which optional amino acids (e.g., -Gly-Ser-) or other amino acid or chemical compound spacers may be included at the termini of the peptides for the purpose of linking the proteins together or to a carrier. For example, useful P4 variant proteins may include one or more of the above-described P4 variant proteins coupled to a carrier protein. Alternatively, a useful P4 variant protein may be present in a fusion protein containing multiple P4 variant proteins, optionally coupled to carrier protein. For these embodiments, the carrier protein is desirably a protein or other molecule that can enhance the immunogenicity of the selected P4 variant protein. Such a carrier may be a larger molecule that also has an adjuvanting effect. Exemplary conventional protein carriers include, without limitation, *E. coli* DnaK protein, galactokinase (galK, which catalyzes the first step of galactose metabolism in bacteria), ubiquitin, α-mating factor, β-galactosidase, and influenza NS-1 protein. Toxoids (i.e., the sequence which encodes the naturally occurring toxin, with sufficient modifications to eliminate its toxic activity) such as diphtheria toxoid and tetanus toxoid, their respective toxins, and any mutant forms of these proteins, such as $CRM_{197}$ (a non-toxic form of diphtheria toxin, see U.S. Pat. No. 5,614,382), may also be employed as carriers. Other carriers include exotoxin A of *Pseudomonas,* heat labile toxin of *E. coli* and rotaviral particles (including rotavirus and VP6 particles). Alternatively, a fragment or epitope of the carrier protein or other immunogenic protein may be used. For example, a hapten may be coupled to a T cell epitope of a bacterial toxin. See U.S. Pat. No. 5,785,973. Similarly a variety of bacterial heat shock proteins, e.g., mycobacterial hsp-70 may be used. Glutathione-S-transferase (GST) is another useful carrier. One of skill in the art can readily select an appropriate carrier for use in this context. The fusion proteins may be formed by standard techniques for coupling proteinaceous materials. Fusions may be expressed from fused gene constructs prepared by recombinant DNA techniques as described below.

Other suitable P4 variant proteins described herein can differ from the specifically exemplified P4 variant proteins or peptides by modifications which do not revive enzymatic activity, and do not diminish immunogenicity, or by combinations of such attributes. For example, conservative amino acid changes may be made, which, although they alter the primary sequence of the P4 variant protein, do not normally alter its function.

In making such changes, the hydropathic index of amino acids can be considered. The importance of the hydropathic amino acid index in conferring interactive biologic function on a polypeptide is generally understood in the art (Kyte & Doolittle, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within +/−2 is preferred, those within +/−1 are particularly preferred, and those within +/−0.5 are even more partcularly preferred.

Substitution of like amino acids can also be made on the basis of hydrophilicity, particularly where the biologically functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred; those within ±1 are particularly preferred; and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

In addition, modifications, which do not normally alter the primary sequence of the P4 variant protein, include in vivo or in vitro chemical derivatization of polypeptides, e.g., acetylation, methylation, or carboxylation. Also included as P4 variant proteins of this invention are these proteins modified by glycosylation, e.g., those made by modifying the glycosylation patterns of a polypeptide during its synthesis and processing or in further processing steps; or by exposing the polypeptide to enzymes which affect glycosylation, such as mammalian glycosylating or deglycosylating enzymes. Also embraced as P4 variant proteins are the above-identified mutagenized sequences, which have phosphorylated amino acid residues, e.g., phosphotyrosine, phosphoserine, or phosphothreonine.

Also included as P4 variant proteins are the above sequences that have been modified using ordinary molecular biological techniques so as to improve their resistance to proteolytic degradation or to optimize solubility properties. Among such P4 variant proteins are included those containing residues other than naturally occurring L-amino acids, e.g., D-amino acids or non-naturally occurring synthetic amino acids. Among other known modifications which may be present in P4 variant proteins of the present invention are, without limitation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, GPI anchor formation, hydroxylation, iodination, methylation, myristoylation, oxidation, proteolytic processing, prenylation, racemization, selenoylation, sulfation, transfer-RNA mediated addition of amino acids to proteins such as arginylation, and ubiquitination.

B. Nucleic Acid Molecules Encoding P4 Variant Proteins

Another aspect of this invention includes isolated, synthetic or recombinant nucleic acid molecules and sequences encoding the above-described P4 variant proteins having the specified site directed mutations or fragments of P4 proteins (which fragments may further contain one or more of those mutations).

An isolated nucleotide molecule comprising a nucleic acid sequence encoding a P4 variant protein may be preferably under the control of regulatory sequences that direct expression of the P4 variant in a host cell. As described herein, such nucleic acid molecules may be used to express the P4 variant protein in vitro or to permit expression of the P4 variant protein in vivo in a human.

As used herein, the term "isolated nucleotide molecule or sequence" refers to a nucleic acid segment or fragment which is free from contamination with other biological components that may be associated with the molecule or sequence in its natural environment. For example, one embodiment of an isolated nucleotide molecule or sequence of this invention is a sequence separated from sequences which flank it in a naturally occurring state, e.g., a DNA fragment which has been removed from the sequences which are normally adjacent to the fragment, such as the sequences adjacent to the fragment in a genome in which it naturally occurs. Further, the nucleotide sequences and molecules of this invention have been altered to encode a P4 variant protein of this invention. Thus, the term "isolated nucleic acid molecule or sequence" also applies to nucleic acid sequences or molecules that have been substantially purified from other components that naturally accompany the unmutagenized nucleic acid, e.g., RNA or DNA or proteins, in the cell. An isolated nucleotide molecule or sequence of this invention also encompasses sequence and molecules that have been prepared by other conventional methods, such as recombinant methods, synthetic methods, e.g., mutagenesis, or combinations of such methods. The nucleotide sequences or molecules of this invention should not be construed as being limited solely to the specific nucleotide sequences presented herein, but rather should be construed to include any and all nucleotide sequences which share homology (i.e., have sequence identity) with the nucleotide sequences presented herein.

The terms "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 70% of the nucleotide bases, as measured by any well-known algorithm of sequence identity, such as Fasta, a program in GCG Version 6.1. The term "homologous" as used herein, refers to the sequence similarity between two polymeric molecules, e.g., between two nucleic acid molecules, e.g., two DNA molecules or two RNA molecules, or between two polypeptide molecules. When a nucleotide or amino acid position in both of the two molecules is occupied by the same monomeric nucleotide or amino acid, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous. If 90% of the positions, e.g., 9 of 10, are matched or homologous, the two sequences share 90% homology. By way of example, the DNA sequences 3'ATTGCC5' and 3'TATGCG5' share 50% homology. By the term "substantially homologous" as used herein, is meant DNA or RNA which is about 70% homologous, more preferably about 80% homologous and most preferably about 90% homologous to the desired nucleic acid.

The invention is also directed to an isolated nucleotide molecule comprising a nucleic acid sequence that is at least 70%, 80% or 90% homologous to a nucleic acid sequence encoding a P4 variant protein of NTHi that has reduced enzymatic activity compared to wild-type P4 protein and that induces antibody to wild-type P4 protein and/or that has bactericidal activity against NTHi, wherein the P4 variant protein has a mutation selected from the group consisting of:

(a) a mutation at amino acid residue 39 of SEQ ID NO:3, which is a glutamine in wild-type P4 protein;
(b) a mutation at amino acid residue 48 of SEQ ID NO:3, which is a phenylalanine in wild-type P4 protein;
(c) a mutation at amino acid residue 64 of SEQ ID NO:3, which is an aspartic acid in wild-type P4 protein;
(d) a mutation at amino acid residue 161 of SEQ ID NO:3, which is a lysine in wild-type P4 protein;
(e) a mutation at amino acid residue 218 of SEQ ID NO:3, which is an asparagine in wild-type P4 protein;
(f) mutations at amino acid residues 35 and 37 of SEQ ID NO:3, which are alanine in wild-type P4 protein, where the mutations are not glutamic acid, glutamine or threonine;
(g) mutations at amino acid residues 64 and 66 of SEQ ID NO:3, which are aspartic acid in wild-type P4 protein; and
(h) combinations of one or more of the mutations of (a)-(g), where the nucleic acid sequence encodes at least one of the mutations of (a)-(g).

Furthermore, due to the degeneracy of the genetic code, any three-nucleotide codon that encodes a mutated amino acid residue of P4, described herein is within the scope of the invention.

Where, as discussed herein, P4 variant proteins and/or DNA sequences encoding them, or other sequences useful in nucleic acid molecules or compositions described herein are defined by their percent homologies or identities to identified sequences, the algorithms used to calculate the percent homologies or percent identities include the following: the Smith-Waterman algorithm (J. F. Collins et al, 1988, Comput. Appl. Biosci., 4:67-72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp. 417), and the BLAST and FASTA programs (E. G. Shpaer et al, 1996, Genomics, 38:179-191). These references are incorporated herein by reference.

By describing two DNAs as being "operably linked" as used herein, is meant that a single-stranded or double-stranded DNA comprises each of the two DNAs and that the two DNAs are arranged within the DNA in such a manner that at least one of the DNA sequences is able to exert a physiological effect by which it is characterized upon the other.

Preferably, for use in producing a P4 variant protein of this invention or administering it for in vivo production in a cell, each P4 variant protein encoding sequence and necessary regulatory sequences are present in a separate viral or non-viral recombinant vector (including non-viral methods of delivery of a nucleic acid molecule into a cell). Alternatively, two or more of these nucleic acid sequences encoding duplicate copies of a P4 variant protein or encoding multiple different P4 variant proteins of this invention may be contained in a polycistronic transcript, i.e., a single molecule designed to express multiple gene products.

By the term "vector" as used herein, is meant a DNA molecule derived from viral or non-viral, e.g., bacterial, species that has been designed to encode an exogenous or heterologous nucleic acid sequence. Thus, the term includes conventional bacterial plasmids. Such plasmids or vectors can include plasmid sequences from viruses or phages. Such vectors include chromosomal, episomal and virus-derived vectors, e.g., vectors derived from bacterial plasmids, bacteriophages, yeast episomes, yeast chromosomal elements, and viruses. Vectors may also be derived from combinations thereof, such as those derived from plasmid and bacteriophage genetic elements, cosmids, and phagemids. The term also includes non-replicating viruses that transfer a gene from one cell to another. The term should also be construed to include non-plasmid and non-viral compounds which facilitate transfer of nucleic acid into cells, such as, for example, polylysine compounds and the like.

The nucleic acid molecules of the invention include non-viral vectors or methods for delivery of the sequence encoding the P4 variant protein to a host cell according to this invention. A variety of non-viral vectors are known in the art and may include, without limitation, plasmids, bacterial vectors, bacteriophage vectors, "naked" DNA and DNA condensed with cationic lipids or polymers.

Examples of bacterial vectors include, but are not limited to, sequences derived from bacille *Calmette Guerin* (BCG), *Salmonella, Shigella, E. coli,* and *Listeria,* among others. Suitable plasmid vectors include, for example, pBR322, pBR325, pACYC177, pACYC184, pUC8, pUC9, pUC18, pUC19, pLG339, pR290, pK37, pKC101, pAC105, pVA51, pKH47, pUB110, pMB9, pBR325, Col E1, pSC101, pBR313, pML21, RSF2124, pCR1, RP4, pBAD18, and pBR328.

Examples of suitable inducible *Escherichia coli* expression vectors include pTrc (Amann et al., 1988 Gene, 69:301-315), the arabinose expression vectors (e.g., pBAD18, Guzman et al, 1995 J. Bacteriol., 177:4121-4130), and pETIId (Studier et al., 1990 Methods in Enzymology, 185:60-89). Target gene expression from the pTrc vector relies on host RNA polymerase transcription from a hybrid trp-lac fusion promoter. Target gene expression from the pETIId vector relies on transcription from a T7 gn10-lac fusion promoter mediated by a coexpressed viral RNA polymerase T7 gn 1. This viral polymerase is supplied by host strains BL21 (DE3) or HMS I 74(DE3) from a resident prophage harboring a T7 gn1 gene under the transcriptional control of the lacUV 5 promoter. The pBAD system relies on the inducible arabinose promoter that is regulated by the araC gene. The promoter is induced in the presence of arabinose.

An exemplary vector is a single or double-stranded bacteriophage vector. For example, a suitable cloning vector includes, but is not limited to the vectors such as bacteriophage λ vector system, λgt11, μgt μWES.tB, Charon 4, λgt-WES-λB, Charon 28, Charon 4A, λgt-1-λBC, λgt-1-λB, M13mp7, M13mp8, or M13mp9, among others.

In another embodiment, the expression vector is a yeast expression vector. Examples of vectors for expression in a yeast such as *S. cerevisiae* include pYepSec I (Baldari, et al., 1987), pMFa (Kurjan and Herskowitz, 1982), pJRY88 (Schultz et al., 1987), and pYES2 (Invitrogen Corporation, San Diego, Calif).

Alternatively, baculovirus expression vectors are used. Baculovirus vectors available for expression of proteins in cultured insect cells (e.g., Sf 9 or Sf 21 cells) include the pAc series (Smith et al., 1983) and the pVL series (Lucklow and Summers, 1989).

In yet another embodiment, a mammalian expression vector is used for expression in mammalian cells. Examples of mammalian expression vectors include pCDM8 (Seed, 1987) and pMT2PC (Kaufman et al., 1987). When used in mammalian cells, the expression vector's control functions are often provided by viral regulatory elements.

One type of recombinant vector is a recombinant single or double-stranded RNA or DNA viral vector. A variety of viral vector systems are known in the art. Examples of such vectors include, without limitation, recombinant adenoviral vectors, herpes simplex virus (HSV)-based vectors, adeno-associated viral (AAV) vectors, hybrid adenoviral/AAV vectors, recombinant retroviruses or lentiviruses, recombinant poxvirus vectors, recombinant vaccinia virus vectors, SV-40 vectors, insect viruses such as baculoviruses, and the like that are constructed to carry or express a selected nucleic acid composition of interest.

Retrovirus vectors that can be employed include those described in EP 0 415 731; International Patent Publication Nos. WO 90/07936; WO 94/03622; WO 93/25698; and WO 93/25234; U.S. Pat. No. 5,219,740; International Patent Publication Nos. WO 93/11230 and WO 93/10218; Vile and Hart, 1993 Cancer Res. 53:3860-3864; Vile and Hart, 1993 Cancer Res. 53:962-967; Ram et al., 1993 Cancer Res. 53:83-88; Takamiya et al., 1992 J. Neurosci. Res. 33:493-503; Baba et al., 1993 J. Neurosurg. 79:729-735; U.S. Pat. No. 4,777,127; GB Patent No. 2,200,651; and EP 0 345 242. Examples of suitable recombinant retroviruses include those described in International Patent Publication No. WO 91/02805.

Alphavirus-based vectors may also be used as the nucleic acid molecule encoding the P4 variant protein. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and International Patent Publication Nos. WO 92/10578; WO 94/21792; WO 95/27069; WO 95/27044; and WO 95/07994.

Examples of adenoviral vectors include those described by Berkner, 1988 Biotechniques 6:616-627; Rosenfeld et al., 1991 Science 252:431-434; International Patent Publication No. WO 93/19191; Kolls et al., 1994 PNAS 91:215-219; Kass-Eisler et al., 1993 PNAS 90:11498-11502; Guzman et al., 1993 Circulation 88:2838-2848; Guzman et al., 1993 Cir. Res. 73:1202-1207; Zabner et al., 1993 Cell 75:207-216; Li et al., 1993 Hum. Gene Ther. 4:403-409; Cailaud et al., 1993 Eur. J. Neurosci. 5:1287-1291; Vincent et al., 1993 Nat. Genet. 5:130-134; Jaffe et al., 1992 Nat. Genet. 1:372-378; and Levrero et al., 1991 Gene 101:195-202. Exemplary adenoviral vectors include those described in International Patent Publication Nos. WO 94/12649; WO 93/03769; WO 93/19191; WO 94/28938; WO 95/11984 and WO 95/00655. Other adenoviral vectors include those derived from chimpanzee adenoviruses, such as those described in U.S. Pat. No. 6,083,716.

Another viral vector is based on a parvovirus such as an adeno-associated virus (AAV). Representative examples include the AAV vectors described in International Patent Publication No. WO 93/09239, Samulski et al., 1989 J. Virol. 63:3822-3828; Mendelson et al.,1988 Virol. 166:154-165; and Flotte et al., 1993 PNAS 90:10613-10617. Other particularly desirable AAV vectors include those based upon AAV1; see, International Patent Publication No. WO 00/28061, published May 18, 2000. Other desirable AAV vectors include those which are pseudotyped, i.e., contain a minigene composed of AAV 5' ITRS, a transgene, and AAV 3' ITRs packaged in a capsid of an AAV serotype heterologous to the AAV ITRs. Methods of producing such pseudotyped AAV vectors are described in detail in International Patent Publication No. WO01/83692.

In an embodiment in which the nucleic acid molecule of the invention is "naked DNA", it may be combined with polymers including traditional polymers and non-traditional polymers such as cyclodextrin-containing polymers and protective, interactive noncondensing polymers, among others. The "naked" DNA and DNA condensed with cationic lipids or polymers are typically delivered to the cells using chemical methods. A number of chemical methods are known in the art for cell delivery and include using lipids, polymers, or proteins to complex with DNA, optionally condensing the same into particles, and delivering to the cells. Another non-viral chemical method includes using cations to condense DNA, which is then placed in a liposome and used according to the present invention. See, C. Henry, 2001 Chemical and Engineering News, 79(48):35-41.

The nucleic acid molecule is introduced directly into the cells either as "naked" DNA (U.S. Pat. No. 5,580,859) or formulated in compositions with agents, which facilitate immunization, such as bupivicaine and other local anesthetics (U.S. Pat. No. 6,127,170).

All components of the viral and non-viral vectors above may be readily selected from among known materials in the art and available from the pharmaceutical industry. Selection of the vector components and regulatory sequences are not considered a limitation on this invention. Each nucleic acid sequence encoding a P4 variant protein according to this invention is preferably under the control of regulatory sequences that direct the replication and generation of the product of each nucleic acid sequence in a mammalian cell. By the term "promoter/regulatory sequence" is meant a DNA sequence required for expression of a nucleic acid operably linked to the promoter/regulatory sequence. In some instances, the promoter/regulatory sequence may function in a tissue specific manner. For example, the promoter/regulatory sequence is only capable of driving expression in a cell of a particular tissue type. In some instances, this sequence may be the core promoter sequence and in other instances, this sequence may also include an enhancer sequence and other regulatory elements that are required for expression in a tissue-specific manner.

Preferably, the nucleic acid molecule encoding a P4 variant protein of this invention and/or the recombinant vector further comprises regulatory sequences. For example, such regulatory sequences comprise a promoter that drives expression of the P4 variant protein. Preferably the promoter/regulatory sequence is positioned at the 5' end of the coding sequence such that it drives expression of the P4 variant protein in a cell.

Suitable promoters may be readily selected from among constitutive promoters, inducible promoters, tissue-specific promoters and others. Examples of constitutive promoters that are non-specific in activity and employed in the nucleic acid molecules encoding the P4 variant protein of this invention include, without limitation, the retroviral Rous sarcoma virus (RSV) promoter, the retroviral LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the $\beta$-actin promoter, the phosphoglycerol kinase (PGK) promoter, and the EF1$\alpha$ promoter (Invitrogen).

Inducible promoters that are regulated by exogenously supplied compounds, include, without limitation, the arabinose promoter, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, 1996 Proc. Natl. Acad. Sci. USA, 93:3346-3351), the tetracycline-repressible system (Gossen et al, 1992 Proc. Natl. Acad. Sci. USA, 89:5547-5551), the tetracycline-inducible system (Gossen et al, 1995 Science, 268:1766-1769, see also Harvey et al, 1998 Curr. Opin. Chem. Biol., 2:512-518), the RU486-inducible system (Wang et al, 1997 Nat. Biotech., 15:239-243 and Wang et al, 1997 Gene Ther., 4:432-441) and the rapamycin-inducible system (Magari et al, 1997 J. Clin. Invest., 100: 2865-2872).

Other types of inducible promoters that may be useful in this context are those regulated by a specific physiological state, e.g., temperature or acute phase or in replicating cells only. Useful tissue-specific promoters include the promoters from genes encoding skeletal $\beta$-actin, myosin light chain 2A, dystrophin, muscle creatine kinase, as well as synthetic muscle promoters with activities higher than naturally-occurring promoters (see Li et al., 1999 Nat. Biotech., 17:241-245). Examples of promoters that are tissue-specific are known for liver (albumin, Miyatake et al. 1997 J. Virol., 71:5124-32; hepatitis B virus core promoter, Sandig et al., 1996 Gene Ther., 3: 1002-9; alpha-fetoprotein (AFP), Arbuthnot et al., 1996 Hum. Gene Ther., 7:1503-14), bone (osteocalcin, Stein et al., 1997 Mol. Biol. Rep., 24:185-96; bone sialoprotein, Chen et al., 1996 J. Bone Miner. Res., 11:654-64), lymphocytes (CD2, Hansal et al., 1988 J. Immunol., 161:1063-8; immunoglobulin heavy chain; T cell receptor $\alpha$ chain), neuronal (neuron-specific enolase (NSE) promoter, Andersen et al. 1993 Cell. Mol. Neurobiol., 13:503-15; neurofilament light-chain gene, Piccioli et al., 1991 Proc. Natl. Acad. Sci. USA, 88:5611-5; the neuron-specific vgf gene, Piccioli et al., 1995 Neuron, 15:373-84); among others. See, e.g., International Patent Publication No. WO00/55335 for additional lists of known promoters useful in this context.

Additional regulatory sequences for inclusion in a nucleic acid sequence, molecule or vector or this invention include, without limitation, an enhancer sequence, a polyadenylation sequence, a splice donor sequence and a splice acceptor sequence, a site for transcription initiation and termination positioned at the beginning and end, respectively, of the polypeptide to be translated, a ribosome binding site for translation in the transcribed region, an epitope tag, a nuclear localization sequence, an IRES element, a Goldberg-Hogness "TATA" element, a restriction enzyme cleavage site, a selectable marker and the like. Enhancer sequences include, e.g., the 72 bp tandem repeat of SV40 DNA or the retroviral long terminal repeats or LTRs, etc. and are employed to increase transcriptional efficiency. Selection of promoters and other common vector elements are conventional and many such sequences are available with which to design the nucleotide molecules and vectors useful in this invention. See, e.g., Sambrook et al, Molecular Cloning. A Laboratory Manual, Cold Spring Harbor Laboratory, New York, (1989) and references cited therein at, for example, pages 3.18-3.26 and 16.17-16.27 and Ausubel et al., Current Protocols in Molecular Biology, John Wiley & Sons, New York (1989). One of skill in the art may readily select from among such known regulatory sequences to prepare molecules of this invention. The selection of such regulatory sequences is not a limitation of this invention.

C. Methods for Making the P4 Variant Proteins and Nucleotide Molecules of this Invention The preparation or synthesis of the nucleotide sequences and P4 variant proteins, as well as compositions containing the nucleotide molecules or P4 variant protein of this invention disclosed herein is well within the ability of the person having ordinary skill in the art using available material. The synthesis methods are not a limitation of this invention. The examples below detail presently preferred embodiments of synthesis of sequences encoding the P4 variant proteins of this invention.

The P4 variant proteins and nucleotide molecules and sequences of this invention may be produced by chemical synthesis methods, recombinant genetic engineering methods, site directed mutagenesis, among others, and combinations of such methods.

For example, the nucleotide sequences/P4 variant proteins of the invention may be prepared conventionally by resort to known chemical synthesis techniques, e.g., solid-phase chemical synthesis, such as described by Merrifield, 1963 J. Amer. Chem. Soc., 85:2149-2154; J. Stuart and J. Young, Solid Phase Peptide Synthesis, Pierce Chemical Company, Rockford, Ill. (1984); Matteucci et al., 1981 J. Am. Chem. Soc., 103:3185; Alvarado-Urbina et al., 1980 Science, 214: 270; and Sinha, N. D. et al., 1984 Nucl. Acids Res., 13:4539, among others. See, also, e.g., PROTEINS-STRUCTURE AND MOLECULAR PROPERTIES, 2nd Ed., T. E. Creighton, W. H. Freeman and Company, New York, 1993; Wold, F., "Posttranslational Protein Modifications: Perspectives and Prospects", pgs. 1-12 in POSTTRANSLATIONAL COVALENT MODIFICATION OF PROTEINS, B. C. Johnson, Ed., Academic Press, New York, 1983; Seifter et al.,1990 Meth. Enzymol., 182:626-646, and Rattan et al., 1992 Ann. N.Y. Acad. Sci., 663:48-62.

Alternatively, compositions of this invention may be constructed recombinantly using conventional molecular biology techniques, site-directed mutagenesis, genetic engineering or polymerase chain reaction, such as, by cloning and expressing a nucleotide molecule encoding a P4 variant protein with optional other immunogens and optional carrier proteins within a host microorganism, etc. utilizing the information provided herein (See, e.g., Sambrook et al., Molecular Cloning. A Laboratory Manual, 2d Edit., Cold Spring Harbor Laboratory, New York (1989); Ausubel et al. Current Protocols in Molecular Biology, John Wiley & Sons, New York (1997)). Coding sequences for the P4 variant proteins and optional immunogens can be prepared synthetically (W. P. C. Stemmer et al, Gene, 164:49 (1995)). Alternatively, DNA encoding P4 wild-type protein may be isolated from *Haemophilus influenzae* as described in U.S. Pat. No. 5,780,601, incorporated herein by reference, and mutagenized.

In general, recombinant DNA techniques involve obtaining by synthesis or isolation a DNA sequence that encodes the P4 variant protein as described above, and introducing it into an appropriate vector/host cell expression system where it is expressed. Any of the methods described for the insertion of DNA into an expression vector may be used to ligate a promoter and other regulatory control elements into specific sites within the selected recombinant vector. Recombinant P4 variant proteins of this invention may be produced as a lipidated or nonlipidated protein by using the P4 leader encoding sequence or no leader sequence (or a leader sequence not specifying fatty acid acetylation as discussed above), respectively.

A variety of host cell-vector systems may be used to express the P4 variant proteins of this invention. Systems for cloning and expressing the P4 variant proteins and other compositions of this invention using the synthetic nucleic acid molecules include the use of various microorganisms and cells which are well known in recombinant technology. The host cell may be selected from any biological organism, including prokaryotic (e.g., bacterial) cells and eukaryotic cells, including, mammalian, insect cells, yeast cells. Preferably, the cells employed in the various methods and compositions of this invention are bacterial cells.

Suitable bacterial cells include, for example, various strains of *E. coli, Bacillus,* and *streptomyces*. Yeast cells such as *Saccharomyces* and *Pichia,* and insect cells such as Sf9 and Sf21 cells are also useful host cells for production purposes. Mammalian cells such as Chinese hamster ovary cells (CHO), NIH3T3, PER C6, NSO, VERO or COS cells are also suitable host cells.

The vector may be selected from one of the viral vectors or non-viral vectors described above but must be compatible with the host cell used. The recombinant DNA vector may be introduced into appropriate host cells (bacteria, virus, yeast, mammalian cells or the like) by transformation, transduction or transfection (depending upon the vector/host cell system). Host-vector systems include but are not limited to bacteria transformed with bacteriophage DNA, plasmid DNA or cosmid DNA; microorganisms such as yeast containing yeast vectors; mammalian cell systems infected with virus (e.g., vaccinia virus, adenovirus, etc.); and insect cell systems infected with virus (e.g., baculovirus).

The selection of other suitable host cells and methods for transformation, culture, amplification, screening and product production and purification can be performed by one of skill in the art by reference to known techniques. See, e.g., Gething and Sambrook, 1981 Nature, 293:620-625, among others.

Typically, the host cell is maintained under culture conditions for a period of time sufficient for expression. Culture conditions are well known in the art and include ionic composition and concentration, temperature, pH and the like. Typically, transfected cells are maintained under culture conditions in a culture medium. Suitable media for various cell types are well known in the art. In a preferred embodiment, temperature is from about 20° C. to about 50° C., more preferably from about 30° C. to about 400C. and, even more preferably about 37° C.

The pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/L and, more preferably from about 290 mosm/L to about 310 mosm/L. Other biological conditions needed for transfection and expression of an encoded protein are well known in the art.

Recombinant P4 variant protein is recovered or collected either from the host cells or membranes thereof or from the medium in which those cells are cultured. Recovery comprises isolating and purifying the recombinant P4 variant protein. Isolation and purification techniques for polypeptides are well known in the art and include such procedures as precipitation, filtration, chromatography, electrophoresis and the like.

When produced by conventional recombinant means, P4 variant proteins of this invention may be isolated and purified from the cell or medium thereof by conventional methods, including chromatography (e.g., ion exchange, affinity, and sizing column chromatography), centrifugation, differential solubility, or by any other standard techniques for the purification or proteins. Several techniques exist for purification of heterologous protein from prokaryotic cells. See, U.S. Pat. Nos. 4,518,526; 4,599,197; and 4,734,362. The purified preparation however produced should be substantially free of host toxins, which might be harmful to humans. In particular, when expressed in gram negative bacterial host cells such as *E. coli*, the purified peptide or protein should be substantially free of endotoxin contamination. See, e.g., Sambrook et al., Molecular Cloning. A Laboratory Manual., 2d Edit., Cold Spring Harbor Laboratory, New York (1989).

The P4 variant proteins used in methods and compositions of the invention are not limited to products of any of the specific exemplary processes listed herein. In fact, the protein may be prepared by the methods in the texts cited immediately above or by methods of the texts cited elsewhere in this specification. It is within the skill of the art to isolate and produce recombinantly or synthetically protein compositions for such use. The resulting composition may be formulated into an immunogenic composition with any number of optional immunogens and screened for efficacy by in vivo assays, such as the BC assay described in the examples below. Alternatively, the proteins and/or nucleotide molecules prepared as described above may be useful in diagnostic assays.

D. Immunogenic Compositions of this Invention

The P4 variant proteins of this invention and the nucleic acid molecules encoding them may be used in a variety of immunogenic compositions, to induce a protective immune response against non-typable H. influenzae. Such immunogenic compositions may be used to prevent or reduce susceptibility to acute otitis media and other diseases caused by NTHi. The immunogenic compositions are useful to generally immunize children or adults against otitis media or they may be useful for children at risk of contracting otitis media (for example, children with a history of ear infection).

These variant P4 proteins of NTHi are also suitable for inclusion in immunogenic compositions against various typable strains of *H. influenzae*, such as *H. influenzae* type b, because the hel gene that encodes the P4 protein is antigenically conserved within and between strains of *H. influenzae*.

Such immunogenic compositions may be formulated as univalent and multivalent vaccines. Such compositions contain in addition to a nucleic acid molecule encoding a P4 variant protein or the protein itself, another antigen or nucleotide molecule expressing that other antigen. Such additional antigens for use in immunogenic compositions of this invention include B or T cell epitopes of other antigens. Among such "other antigens" for co-administration with a P4 variant protein of this invention are included, without limitation, other antigens of *H. influenzae,* such as other outer membrane proteins of *H. influenzae* (or peptides or proteins having epitopes thereof. Such outer membrane proteins of *H. influenzae* include the 15,000-dalton peptidoglycan-associated outer membrane lipoprotein (PAL) and the 15,000-dalton *Haemophilus* lipoprotein PCP (Deich, R. A. et al. 1988 J. Bacteriol. 170(2):489-498). The "other" antigen may also include oligo- or polysaccharide capsular components of *H. influenzae,* such as polyribosylribitolphosphate (PRP), or lipopolysaccharide, lipooligosaccharide or liposaccharide components of *H. influenzae* or other microorganisms. Additional "other" antigens that may be included in the immunogenic compositions of this invention include antigens of other organisms (e.g. encapsulated or nonencapsulated, bacteria, viruses, fungi and parasites). For example, antigens of other microorganisms implicated in otitis media, such as *Streptococcus pneumoniae* (including, but nor limited to, one or more known *Streptococcus pneumoniae* polypeptides, lipopolysaccharide-protein conjugates and polysaccharide-protein conjugates, including, but not limited to, the currently available 23-valent pneumococcal capsular polysaccharide vaccine and the 7-valent pneumococcal polysaccharide-protein conjugate vaccine), *Streptococcus pyogenes* group A, Staphylococcus aureus, respiratory syncytial virus and *Moraxella catarrhalis* (including, but nor limited to, the UspA1, UspA2, B1, C/D, E and 74 kDa proteins) may be included in the immunogenic compositions of this invention.

1. Use of P4 Variant Proteins in Immunogenic Compositions

The P4 variant proteins are desirably formulated into immunogenic compositions for induction of a protective immune response. Thus, in one embodiment, an immunogenic composition of this invention contains one or more of the P4 variant proteins as described above, in a pharmaceutically acceptable carrier. Such formulations comprise the P4 variant protein combined with a pharmaceutically acceptable carrier, such as sterile water or sterile isotonic saline. As used herein the language "pharmaceutically acceptable carrier" is intended to include any and all solvents, dispersion media, coatings, antibacterial and antifungal agents, isotonic and absorption delaying agents, and the like, compatible with administration to humans. The appropriate carrier will be evident to those skilled in the art and will depend in large part upon the route of administration.

Formulations include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. Other parenterally-administrable formulations, which are useful, include those, which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Still additional components that may be present in the protein immunogenic compositions of this invention are adjuvants, preservatives, chemical stabilizers, or other antigenic proteins. Typically, stabilizers, adjuvants, and preservatives are optimized to determine the best formulation for efficacy in the target human or animal. Suitable exemplary preservatives include chlorobutanol, potassium sorbate, sorbic acid, sulfur dioxide, propyl gallate, the parabens, ethyl vanillin, glycerin, phenol, and parachlorophenol. Suitable stabilizing ingredients that may be used include, for example, casamino acids, sucrose, gelatin, phenol red, N-Z amine, monopotassium diphosphate, lactose, lactalbumin hydrolysate, and dried milk.

A conventional adjuvant is used to enhance an immune response. Such adjuvants include, among others, MPL™ (3-O-deacylated monophosphoryl lipid A; Corixa, Hamilton, Mont.), which is described in U.S. Pat. No. 4,912,094, which is hereby incorporated by reference.

Also suitable for use as adjuvants are aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino] ethyl 2-Deoxy-4-O-phosphono-3-O-[(R)-3-tetradecanoyoxytetradecanoyl]-2-[(R)-3-tetradecanoyoxytetradecanoylamino]-b-D-glucopyranoside, which is also known as 529 (formerly known as RC529). This 529 adjuvant is formulated as an aqueous form or as a stable emulsion.

Other adjuvants include mineral oil and water emulsions, aluminum salts (alum), such as aluminum hydroxide, aluminum phosphate, etc., Amphigen, Avridine, L121/squalene, D-lactide-polylactide/glycoside, pluronic polyols, muramyl dipeptide, killed Bordetella, saponins, such as Quil A or Stimulon™ QS-21 (Antigenics, Framingham, Mass.), described in U.S. Pat. No. 5,057,540, which is hereby incorporated by reference, and particles generated therefrom such as ISCOMS (immunostimulating complexes), Mycobacterium tuberculosis, bacterial lipopolysaccharides, synthetic polynucleotides such as oligonucleotides containing a CpG motif (U.S. Pat. No. 6,207,646, which is hereby incorporated by reference), cholera toxin (either in a wild-type or mutant form, e.g., wherein the glutamic acid at amino acid position 29 is replaced by another amino acid, preferably a histidine, in accordance with International Patent Publication No. WO 00/18434, incorporated herein by reference), a pertussis toxin (PT), or an E. coli heat-labile toxin (LT), particularly LT-K63, LT-R72, CT-SI09, PT-K9/G129; see, e.g., International Patent Publication Nos. WO 93/13302 and WO 92/19265, incorporated herein by reference. Various cytokines and lymphokines are suitable for use as adjuvants. One such adjuvant is granulocyte-macrophage colony stimulating factor (GM-CSF), which has a nucleotide sequence as described in U.S. Pat. No. 5,078,996, which is hereby incorporated by reference. A plasmid containing GM-CSF cDNA has been transformed into E. coli and has been deposited with the American Type Culture Collection (ATCC), 10801 University Boulevard, Manassas, Va. 20110-2209, under Accession Number 39900. The cytokine Interleukin-12 (IL-12) is another adjuvant that is described in U.S. Pat. No. 5,723,127, which is hereby incorporated by reference. Other cytokines or lymphokines have been shown to have immune modulating activity, including, but not limited to, the interleukins 1-alpha, 1-beta, 2, 4, 5, 6, 7, 8, 10, 13, 14, 15, 16, 17 and 18, the interferons-alpha, beta and gamma, granulocyte colony stimulating factor, and the tumor necrosis factors alpha and beta, and are suitable for use as adjuvants.

Other suitable adjuvants include, but are not limited to: surface active substances (e.g., hexadecylamine, octadecylamine, octadecyl amino acid esters, lysolecithin, dimethyldioctadecylammonium bromide), methoxyhexadecylglycerol, and pluronic polyols; polyamines, e.g., pyran, dextransulfate, poly IC, carbopol; peptides, e.g., muramyl dipeptide, dimethylglycine, tuftsin; oil emulsions; and mineral gels, e.g., aluminum phosphate, etc. and immune stimulating complexes. The immunogen may also be incorporated into liposomes, or conjugated to polysaccharides, lipopolysaccharides and/or other polymers for use in a vaccine formulation.

As described above, an additional immunogenic component may include one or more optional additional antigens, as described above. For combined administration with epitopes of other outer membrane proteins, the P4 variant protein may be present separately in admixture with the other antigens or it may be present as a conjugate or as a fusion protein comprising multiple outer membrane protein determinants or multiple antigenic determinants with other H. influenzae or non-H. influenzae antigens. For example, the H. influenzae PAL and PCP or any proteins, peptides or epitopes derived from them, may be administered as a mixture or as a conjugate or fusion with a P4 variant protein of this invention.

In formulating the immunogenic compositions with the P4 variant proteins of this invention, alone or in the various combinations described, the immunogen is adjusted to an appropriate concentration and formulated with any suitable adjuvant. In some preferred embodiments, the protein immunogenic composition of the invention is prepared for administration to human subjects in the form of, for example, liquids, powders, aerosols, tablets, capsules, enteric-coated tablets or capsules, or suppositories.

2. Immunogenic Compositions Containing Nucleic Acid Molecules

Another embodiment of an immunogenic composition of this invention comprises a nucleic acid molecule encoding a P4 variant protein of this invention and a pharmaceutically acceptable carrier. The nucleic acid sequences encoding a P4 variant protein for use in an immunogenic composition against NTHi may be present in a suitable pharmaceutically-, or physiologically acceptable carrier, such as isotonic saline or isotonic salts solution. The appropriate carrier will be evident to those skilled in the art and will depend in large part upon the route of administration.

Alternatively, immunogenic compositions composed of polynucleotide molecules desirably contain optional polynucleotide facilitating agents or "co-agents", such as a local anesthetic, a peptide, a lipid including cationic lipids, a liposome or lipidic particle, a polycation such as polylysine, a branched, three-dimensional polycation such as a dendrimer, a carbohydrate, a cationic amphiphile, a detergent, a benzylammonium surfactant, or another compound that facilitates polynucleotide transfer to cells. Non-exclusive examples of such facilitating agents or co-agents useful in this invention are described in U.S. Pat. Nos. 5,593,972; 5,703,055; 5,739,118; 5,837,533; International Patent Publication No. WO96/10038, published Apr. 4, 1996; and International Patent Publication No. WO94/16737, published Aug. 8, 1994, which are each incorporated herein by reference.

Most preferably, the local anesthetic is present in an amount that forms one or more complexes with the nucleic acid molecules. When the local anesthetic is mixed with nucleic acid molecules or plasmids of this invention, it forms a variety of small complexes or particles that pack the DNA and are homogeneous. Thus, in one embodiment of the immunogenic compositions of this invention, the complexes are formed by mixing the local anesthetic and at least one plasmid of this invention. Any single complex resulting from this mixture may contain a variety of combinations of the different plasmids.

Alternatively, in another embodiment of the compositions of this invention, the local anesthetic may be pre-mixed with each plasmid separately, and then the separate mixtures combined in a single composition to ensure the desired ratio of the plasmids is present in a single immunogenic composition, if all plasmids are to be administered in a single bolus administration. Alternatively, the local anesthetic and each plasmid may be mixed separately and administered separately to obtain the desired ratio. Where, hereafter, the term "complex" or "one or more complexes" or "complexes" is used to define this embodiment of the immunogenic composition, it is understood that the term encompasses one or more complexes with each complex containing a mixture of the P4 variant protein-encoding plasmids, or a mixture of complexes formed discretely, wherein each complex contains only one type of plasmid, or a one or a mixture of complexes wherein each complex contains a polycistronic DNA.

Preferably, the complexes are between about 50 to about 150 nm in diameter. When the facilitating agent used is a local anesthetic, preferably bupivacaine, an amount of from about 0.1 weight percent to about 1.0 weight percent based on the total weight of the polynucleotide composition is preferred. See, also, International Patent Publication No. WO99/21591, which is hereby incorporated by reference, and which teaches the incorporation of benzylammonium surfactants as co-agents, preferably administered in an amount of between about 0.001-0.03 weight %. According to the present invention, the amount of local anesthetic is present in a ratio to said nucleic acid molecules of 0.01-2.5% w/v local anesthetic to 1-10 µg/ml nucleic acid. Another such range is 0.05-1.25% w/v local anesthetic to 100 µg/ml to 1 ml/ml nucleic acid.

In this polynucleotide immunization procedure, the variant P4 proteins of the invention are expressed on a transient basis in vivo; no genetic material is inserted or integrated into the chromosomes of the host. This procedure is to be distinguished from gene therapy, where the goal is to insert or integrate the genetic material of interest into the chromosome. An assay is used to confirm that the polynucleotides administered by immunization do not rise to a transformed phenotype in the host (U.S. Pat. No. 6,168,918).

The immunogenic compositions may also contain other additives suitable for the selected mode of administration of the composition. The composition of the invention may also involve lyophilized polynucleotides, which can be used with other pharmaceutically acceptable excipients for developing powder, liquid or suspension dosage forms. See, e.g., Remington: The Science and Practice of Pharmacy, Vol. 2, 19$^{th}$ edition (1995), e.g., Chapter 95 Aerosols; and International Patent Publication No. WO99/45966, the teachings of which are hereby incorporated by reference. Routes of administration for these compositions may be combined, if desired, or adjusted.

Optionally, as described above, these nucleic acid molecule-containing immunogenic compositions can include nucleic acid sequences encoding one or more of the above-noted "additional" antigens. For example, individual nucleotide molecules encoding individual antigens may be admixed with the nucleotide molecule that contains the sequence encoding the P4 variant protein. Alternatively, the sequence encoding the P4 variant protein may be fused to DNA sequence encoding one or more of the other antigens of *H. influenzae* or antigens of other bacteria, viruses, parasites or fungi to create genetically fused (sharing a common peptide backbone) multivalent antigens.

These nucleic acid molecule-containing immunogenic compositions can contain additives suitable for administration via any conventional route of administration. In some preferred embodiments, the immunogenic composition of the invention is prepared for administration to human subjects in the form of, for example, liquids, powders, aerosols, tablets, capsules, enteric-coated tablets or capsules, or suppositories.

3. Recombinant Virus-Containing Immunogenic Compositions

In yet a further aspect of this invention, immunogenic compositions can contain a recombinant virus that is capable of expressing the P4 variant protein (and/or any additional immunogen). Suitable non-pathogenic viruses which may be engineered to carry the nucleic acid molecule of this invention into the cells of the host include poxviruses, such as vaccinia, adenovirus, adeno-associated viruses, canarypox viruses, retroviruses and the like. Preferably, for administration, the virus is a non-replicating virus, such as an E1-deleted adenovirus, typical of those used in gene therapy. See, as an example, the recombinant replication defective adenovirus described in U.S. Pat. No. 5,698,202, among others. A number of such non-pathogenic viruses are commonly used for human gene therapy, and as carriers for other vaccine agents, and are known and selectable by one of skill in the art.

Preferably, the non-replicating virus bearing a nucleic acid sequence encoding a P4 variant protein of this invention is suspended in a biologically compatible solution or pharmaceutically acceptable delivery vehicle. A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, this type of immunogenic composition of the invention may be formulated to contain other components, including, e.g. adjuvants, stabilizers, pH adjusters, preservatives as mentioned above. Such components are well known to those of skill in the vaccine art.

Still a further embodiment suitable for an immunogenic composition according to this invention is the use of inactivated immunogenic compositions, e.g., large quantities of the recombinant virus expressing the desired P4 variant proteins are grown in culture to provide the necessary quantity of relevant antigens and inactivated by conventional means. A mixture of inactivated viruses express different epitopes may be used for the formulation of "multivalent" immunogenic compositions, as described in U.S. Pat. No. 5,780,601, incorporated herein by reference. This immunogenic composition should also contain a suitable adjuvant, as described above, in order to enhance the immunological response to the antigens.

4. Commensal Bacterium-Containing Immunogenic Compositions

In still another aspect of the present invention, the synthetic nucleic acid molecules of this invention that encode the P4 variant protein (including any fusion protein and/or additional antigen) may be incorporated into a non-pathogenic microorganism. The resulting microorganism, when administered to a human host, expresses and multiplies the expressed compositions of this invention in vivo to induce specific antibody formation. For example, a non-pathogenic commensal bacterium can be employed to carry the P4 variant protein-encoding molecules of this invention and is useful for administration to a patient may be prepared by use of conventional methodology and selected from among known non-pathogenic microorganisms. Among commensal bacterium which may be useful for exogenous delivery of the nucleic acid molecule of this invention to the patient in vivo, include, without limitation, various strains of *Streptococcus*, e.g., *S. gordonii*, or *E. coli*, *Bacillus*, *Streptomyces*, and *Saccharomyces*.

The immunogenic compositions of the present invention, as described above, are not limited by the selection of the conventional, physiologically acceptable, carriers, adjuvants, or other ingredients useful in pharmaceutical preparations of the types described above. The preparation of these pharmaceutically acceptable compositions, from the above-described components, having appropriate pH isotonicity, stability and other conventional characteristics is within the skill of the art.

E. Methods of Use

The immunogenic compositions described above may be employed in a method for inducing an immune response in a human against non-typable *H. influenzae* . In one embodiment of this method, an effective amount of a P4 variant protein immunogenic composition as described above is administered to a patient. The amount of the P4 protein, P4 variant-expressing nucleic acid molecule, or P4 variant-expressing recombinant virus in the composition is that amount effective to elicit an immune response against NTHi. Preferably, the immune response is protective against NTHi infection.

Routes of administration for the immunogenic compositions of this invention include, without limitation, parenteral administration, intraperitoneal administration, intravenous administration, intramuscular administration, subcutaneous administration, intradermal administration, oral administration, topical administration, intranasal administration, intrapulmonary administration, rectal administration, vaginal administration, and the like. All such routes are suitable for administration of these compositions. The appropriate route is selected depending on the nature of the immunogenic composition used, and an evaluation of the age, weight, sex and general health of the patient and the antigens present in the immunogenic composition, and similar factors by an attending physician.

In general, selection of the appropriate "effective amount" or dosage for the immunogenic compositions of the present invention will also be based upon the particular immunogenic composition employed, as well as the physical condition of the subject, most especially including the general health and weight of the immunized subject. Such selection and upward or downward adjustment of the effective dose is within the skill of the art. The amount of active component required to induce an immune response, preferably a protective response, or produce an exogenous effect in the patient without significant adverse side effects varies depending upon the pharmaceutical composition employed and the optional presence of an adjuvant (for the protein-containing compositions).

In one embodiment, for the compositions containing protein components, e.g., a P4 variant protein or fusion proteins as described above, each dose will comprise between about 1 μg to about 20 mg of the protein immunogens per mL of a sterile solution. Other dosage ranges may also be contemplated by one of skill in the art. Initial doses may be optionally followed by repeated boosts, where desirable.

In another embodiment, the amounts of nucleotide molecules in the DNA and vector compositions may be selected and adjusted by one of skill in the art. In one embodiment, each dose will comprise between about 50 μg to about 1 mg of immunogen-encoding nucleic acid, e.g., DNA plasmid, per mL of a sterile solution.

For recombinant, preferably replication-defective, viruses containing the nucleic acid molecules encoding the P4 variant proteins of this invention, the "effective amount" is an amount of recombinant virus that is effective in a route of administration to transfect the desired cells of the subject and provide sufficient levels of expression of the selected gene to provide a benefit, i.e., protective immunity. The levels of immunity can be monitored to determine the need, if any, for boosters. However, it is understood that one of skill in the art may alter such dosages depending upon the identity of the recombinant virus and the make-up of the immunogens (i.e., the presence of additional P4 variant proteins or "other antigens" that the recombinant virus is delivering to the host).

The amounts of the commensal bacteria carrying a nucleic acid sequence expressing a P4 variant protein to be delivered to the patient will generally range between about $10^3$ to about $10^{12}$ cells/kg. These dosages may be altered by one of skill in the art depending upon the bacterium being used and the additional P4 variant proteins or "other antigens" being delivered to the host by the live bacterium.

F. Use of P4 Variants as Carrier Proteins

In addition to its utility as a primary immunogen, P4 variant protein may be used as a carrier protein to confer or enhance immunogenicity of other antigens, where the other antigen may be a protein, polypeptide, peptide, polysaccharide, oligosaccharide, saccharide, lipopolysaccharide, lipooligosaccharide or liposaccharide. The variant P4 protein has reduced enzymatic activity compared to wild-type P4 protein, but need not necessarily either induce antibody to wild-type P4 protein or have bactericidal activity against NTHi, with the proviso that the P4 variant carrier protein does not have a phenylalanine at amino acid position 122 of SEQ ID NO:3. For example, the P4 variant protein is chemically conjugated by conventional means to a polysaccharide or lipopolysaccharide or expressed as a fusion protein with another protein.

G. Diagnostic Assays

The P4 variant proteins and nucleic acid molecules of this invention, optionally associated with detectable labels or with components able to detect formation of the immune complex or DNA hybridizations, may also be used as antigens in assays for the detection of non-typable H. influenzae in various tissues and body fluids, e.g., blood, spinal fluid, sputum, etc. These assays and assay formats are conventional and would be the same formats as described for use of wild-type P4 reagents, as described in U.S. Pat. No. 5, 780,601.

For example, the P4 variant proteins of this invention may be employed as reagents in radioimmunoassays, ELISA assays, "sandwich" assays, precipitin reactions, gel diffusion precipitin reactions, immunodiffusion assays, agglutination assays, fluorescent immunoassays, protein A immunoassays and immunoelectrophoresis assays. The P4 variant protein of this invention is optionally associated with a detectable label.

The nucleic acid molecules encoding a P4 variant protein of this invention or any nucleotide sequences which hybridize therewith may be also used as probes in nucleic acid hybridization assays for the detection of non-typable *H. influenzae* , in various tissues or body fluids of patients. Suitable hybridization assays include, without limitation, Southern blots, Northern blots, and colony blots, among others. Stringency of hybridization may be varied depending on the requirements of the assay.

Suitable detectable labels include, without limitation, a protein or small chemical molecule that is capable, acting alone, or in concert with other molecules or proteins, of providing a signal, that is detectable either directly or indirectly. For example, a detectable label can be a fluorescent label, a luminescent label, a radiolabel, or a chemiluminescent label. A label can also be an enzyme that interacts with a substrate to produce a detectable signal. See, e.g., Handbook of Fluorescent Probes and Research Chemicals, 6th Ed., R. P. Haugland, Molecular Probes, Inc., Eugene, Oreg. (1996); U.S. Pat. Nos. 4,542,104 and 5,272,257. Still other labels include the green fluorescent proteins and blue fluorescent proteins. Suitable labels for the nucleic acid molecules can be DNA sequences encoding a lux gene, beta-lactamase, a galactosidase enzyme, e.g., beta-galactosidase (LacZ), alkaline phosphatase, thymidine kinase, green fluorescent protein (GFP), chloramphenicol acetyltransferase (CAT), a luciferase enzyme, or a gluconase enzyme.

Any number of additional, and conventionally employed, marker systems may be adapted for association with the P4 variant proteins and/or nucleic acid sequences encoding the P4 variant proteins of this invention. One of skill understands that selection and/or implementation of a label system involves only routine experimentation.

EXAMPLES

The following examples are provided to illustrate the production and activity of representative P4 variant proteins of this invention. The examples presented here show construction of isolated nucleotide molecules encoding the P4 variant proteins, recombinant expression in host cells, and purification therefrom. The purified proteins were analyzed for enzymatic activity in a sensitive calorimetric assay. The proteins were also used to immunize Swiss-Webster mice, along with wild-type rLP4 and the resulting antisera were analyzed for total IgG antibodies against wild-type rLP4 and bactericidal activity against NTHi. These examples demonstrate that determining which mutants of P4 lack enzymatic activity, while retaining wild-type immunogenicity and elicitation of functional antibodies is not a trivial matter. Three of the mutant P4 proteins constructed as described below possess the desired immunologic properties, namely, eliciting both high ELISA titers against wild-type P4 and high levels of bactericidal antibodies against NTHi. One skilled in the art will appreciate that although specific reagents and conditions are outlined in the following examples, these reagents and conditions are not a limitation on the present invention.

Example 1

Site Directed Mutagenesis of P4 Gene

Bacterial acid phosphatases have been well studied over the years, and have been divided into multiple classes based on their substrate specificity, cellular location, etc. (Thaller, M. C. et al, 1998. Prot. Sci., 7:1647-52.9). Regions with highly conserved amino acids between multiple bacterial acid phosphatases have been identified as likely areas for site directed mutagenesis to eliminate or reduce enzymatic activity, and by making conservative changes, maintain tertiary structure.

Site directed mutagenesis was performed on wild-type P4 after synthetic primers were used to introduce BsmB1 sites and the desired mutations as described below. Digestion with BsmB1 and religation resulted in the desired mutant P4 sequence with the concomitant loss of the BsmB1 site. These lipidated mutant proteins were expressed in E. coli BLR host cells, and purified by slight modification of the standard procedure used to purify lipidated wild-type rLP4.

Specifically, a double aspartic acid site directed mutant was constructed based on information that two aspartic acid residues in the wild-type P4 protein were critical to acid phosphatase activity. A mutant designated P4-351 was constructed in which the amino acid residues at positions Asp64 and Asp66 of SEQ ID NO: 3 were changed to Ala64 and Ala66A. Another mutant designated P4-D184A, D185A was constructed in which the wild-type Asp184 and Asp185 of SEQ ID NO: 3 were mutated to Ala184 and Ala185. In other mutants, site directed mutagenesis of the amino acid residues 35 and 37 of SEQ ID NO: 3 resulted in four proteins, changing the alanine acid residue to either glutamic acid (A35G, A37G), threonine (A35T, A37T), asparagine (A35D, A37D), or glutamine (A35Q, A37Q). These mutants were constructed to determine if changes in another region other than Asp to Ala would result in less conformational disruption of the protein molecule and thus better immunogenicity against wild-type P4.

Additionally, the following single mutations in the P4 protein were made to generate P4 variant proteins N218Q, K161R, D64E, Y122F, D64N, D64E, and Q39E. In addition, a Phe residue at position 48 was changed to a Cys residue. This residue was selected for mutagenesis based on its position in a putative hemin binding domain.

This variety of expressed mutant proteins were produced as identified in Table 1.

TABLE 1

The mutant P4 variant proteins and mutations.

| Name of Mutant P4 | Wild-type amino acid residue(s) | Mutagenized amino acid residue(s) |
|---|---|---|
| F48C | Phe48 | Cys48 |
| F48S | Phe48 | Ser 48 |
| D64A, D66A | Asp64, Asp66 | Ala64, Ala66 |
| K161R | Phe161 | Arg161 |
| N218Q | Asn218 | Gln218 |
| D64N | Asp64 | Asn64 |
| D64E | Asp64 | Glu64 |
| D184A, D185A | Asp184, Asp185 | Ala184, Ala185 |
| A35E, A37E | Ala35, Ala37 | Glu35, Glu37 |
| A35T, A37T | Ala35, Ala37 | Thr35, Thr37 |
| A35N, A37N | Ala35, Ala37 | Asn 35, Asn 37 |
| A35Q, A37Q | Ala35, Ala37 | Gln 35, Gln 37 |
| Q39E | Gln39 | Glu39 |
| Y122F | Tyr122 | Phe122 |

All site directed mutants with the exception of F48C and D64A, D66A were derived from plasmid pLP339, a pBAD18Cam expression vector containing the wild-type non-typable H. influenzae (NTHi) P4 gene (Green, B. A., et al 1991 Infect. Immun., 59:3191-3198) under control of the arabinose promoter. Mutant proteins D64A, D66A and F48C were derived from plasmid pHel3 (Reilly et al, 1999, cited above).

Most of the site directed mutant proteins were constructed using the QuickChange mutagenesis kit (Stratagene) according to the manufacturer's directions. Primers used to construct the P4 mutations are listed in Table 2 below. Oligonucleotide primers used herein, (with the exception of those used by Reilly et al, 1999, cited above), were synthesized on a PerSeptive Biosystems oligonucleotide synthesizer (Applied Biosystems, Foster City, Calif.) using β-cyanoethylphosphoramidite chemistry.

TABLE 2

Primers used for site directed mutagenesis of hel gene.

| Mutation | Sequence (5' to 3') | SEQ ID NOS |
|---|---|---|
| F48C | GCAAAAGTTGCATGCGATCACGCAAAAG | 4 |
|  | CTTTTGCGTGATCGCATGCAACTTTTGC | 5 |
| D64A & D66A | GCGGTTGTGGCTGCTTTAGCTGAAACTATGTTAG | 6 |
|  | CTAACATAGTTTCAGCTAAAGCAGCCACAACCGC | 7 |

TABLE 2-continued

Primers used for site directed mutagenesis of hel gene.

| Mutation | Sequence (5' to 3') | SEQ ID NOS |
|---|---|---|
| K161R | GCGCGTCTCTTGCATTTTATTTGAAAAAAGACAAATCA GCTAGAGCGGCTC | 8 |
|  | GCGCGTCTCGTGCAGATTCTTCCACGCCATTGAAACC | 9 |
| N218Q | GCGCGTCTCTGCTGGGAAGGCGGTTTAGCTGAAG | 10 |
|  | GCGCGTCTCGCAGCCACCGTAGTTTGCTTGAGGTAAC ATGATGAAAG | 11 |
| D64N | GCGCGTCTCTGGTAAGAAAAAAGCGGTTGTGGCTAAT TTAGATG | 12 |
|  | GCGCGTCTCGTACCTTTTGCCACTTTTGCGTG | 13 |
| D64E | GCGCGTCTCGTACCTTTTGCCACTTTTGCGTG | 14 |
|  | GCGCGTCTCTGGTAAGAAAAAAGCGGTTGTGGCTGAA TTAGATG | 15 |
| D184A & D185A | CGCCGTCTCGCTGCCTTCGGTAATACCGTATATGGC | 16 |
|  | CGCCGTCTCGGCAGCTAAGTTATCACCTACATAAAGT ACG | 17 |
| A35E & A37E | CGCCGTCTCTTAGAATATCAAGCGTACAATGCGGC | 18 |
|  | CCGCGTCTCATCTAATTCTTTATATTCGCCAGAATCTT GC | 19 |
| A35N & A37N | GCCCGTCTCCCTTAAACTATCAAGCGTACAATGCGGC | 20 |
|  | GCCCGTCTCCTAAGTTTTATATTCGCCAGAATCTTGC | 21 |
| A35Q & A37Q | CCGCGTCTCATTACAATATCAAGCGTACAATGCGGC | 22 |
|  | GCCCGTCTCGGTAATTGTTTATATTCGCCAGAATCTTG C | 23 |
| A35T & A37T | CGGCGTCTCCATTAACTTATCAAGCGTACAATGCGGC | 24 |
|  | CGGCGTCTCCTAATGTTTTATATTCGCCAGAATCTTGC | 25 |
| Q39E | GCATTAGCTTATGAAGCGTACAATGCGG | 26 |
|  | CCGCATTGTACGCTTCATAAGCTAATGC | 27 |
| Y122F | CGGTAAAGTGTTCTTTGTAACAAACCGC | 28 |
|  | GCGGTTTGTTACAAAGAACACTTTACCG | 29 |

BsmBI seamless cloning was used to generate several of the P4 mutants. Sections of the P4 gene were amplified by polymerase chain reaction (PCR) (PE 2400 thermal cycler, Applied Biosystems, Foster City, Calif.) from plasmid pLP339. First, a primer containing a BsmBI site and the desired mutation was paired with the appropriate vector primer and used to amplify a section of the P4 gene. Additionally, a second primer containing a BsmBI site was paired with an appropriate vector primer and used to amplify the remaining section of the P4 gene. Each section of the P4 gene was ligated and cloned into pCR2.1-TOPO (Invitrogen).

Transformants were screened by PCR for the presence of an insert and confirmed by sequence analysis. Correct clones were restriction digested with BsmBI and SacI or SphI (restriction enzymes supplied by New England Biolabs) and the inserts were purified on low melting point agarose gels. Gel purified fragments were seamlessly ligated together at the BsmBI sites.

Mutagenized P4 genes that were cloned into pCR2.1-TOPO were subcdoned into pBAD18Cam (Invitrogen) for expression of the mutant P4 protein using the SacI-SphI sites, with the exception of the F48C gene. The F48C sequence was subcloned into pBAD18Cam using NheI-SacI sites.

Example 2

Expression of Lipidated Recombinant Mutant P4 Proteins

Plasmids containing these mutant P4 proteins were transformed into E. coli strain BLR and all mutant P4 proteins were expressed recombinantly therein. Clones were confirmed by sequencing of the P4 gene. Overnight cultures of BLR containing the appropriate plasmid were grown in Hy-Soy media buffered with $NaPO_4$ containing 0.05% glucose and 30 µg/ml chloramphenicol at 37° C. with aeration. Flasks containing the same medium minus the glucose were inoculated with a 1:20 dilution of the overnight culture and incubated at 37° C. with aeration until the $OD_{600}$ reached approximately 2.0. The bacteria were then induced with 0.5% arabinose and incubation was continued for 3 hours. Bacterial cells were harvested by centrifugation at 10,0000×g, 4° C., for 30 minutes, and the cell pellets washed 1× with PBS. The cells were repelleted and stored frozen at −20° C. Expression of P4 protein was checked by SDS-PAGE analysis of whole cell lysates using 12% gels.

Example 3

Purification of Lipidated Recombinant P4 and Mutants

The P4 mutant proteins were then purified as follows: The E. coli cells were suspended in hypotonic buffer (10 mM HEPES-NaOH, pH 7.4, 1 mM $Na_2EDTA$) and lysed under high pressure (approximately 18,000 psi) by passing the cell suspension through a microfluidizer. Membranes were obtained following ultracentrifugation for 1 hr at 300,000×g at 10° C. in a Beckman 45Ti rotor. Inner and outer membrane proteins were differentially solubilized by sequential extractions with 1% (w/v) Triton X-100 in 10 mM HEPES-NaOH, pH 7.4, 1 mM $MgCl_2$ and 1% (w/v) Zwittergent 3-12 in 50 mM Tris-HCl, pH8, 5 mM $Na_2EDTA$, respectively. Zwittergent 3-12 extracts solubilized the rLP4 or mutant proteins.

The proteins of interest were purified by fractionation on tandem ion-exchange columns (DEAE & SP-sepharose). The rLP4 protein elutes from the SP-Sepharose in a 0-0.2 M salt gradient as two peaks designated Form 1 and Form 2. Form 2 is converted to Form 1 by slow freezing in a buffer of 10 mM Na phosphate, pH 7.1, 150 mM NaCl, 1% Zwittergent 3-12, followed by dialysis into Tris-EDTA-Zwittergent 3-12 buffer, pH 8. The converted Form 1 is further purified on an SP-sepharose column. The rLP4-mutants were purified by the same method as wild-type protein, except where the mutation reduced the pI of the protein. In these cases, following extraction the buffer was changed to 10 mM HePES-NaOH, pH 7.4, 1 mM Na2EDTA, 1% (w/v) Zwittergent 3-12 prior to the tandem column step. This buffer was also used for elution from the SP-Sepharose column. Most of the rLP4 mutants eluted in a single peak of protein. Protein was assayed using the bicinchoninic acid assay according to the manufacturer's directions (Pierce).

Example 4

Assay for Phosphatase Activity

The purified P4 mutant proteins were then examined for enzymatic activity in a sensitive fluid phase assay. The phosphomonoesterase activity of rLP4 was measured in comparison to wild-type rLP4 by an essentially colorimetric assay as described by Reilly et al. 1999 cited above. The addition of 1% (w/v) Triton X100 to the assay buffer enhanced the activity of rLP4. The nmol amount of p-nitrophenol produced was determined by comparing the absorbance at 410 nm to that of the p-nitrophenol standard curve. One unit of enzyme activity was defined as the amount of activity required to convert 1 μmol of substrate to product per minute at 37° C. The specific activity was defined as the number of units of enzyme per 1 mg protein. Results are also expressed as % of wild-type activity. The results are shown in Table 3.

TABLE 3

Specific Activity of rLP4 Mutants (pNPP assay)

| Mutant | Unit/mg | % of wt[a] |
|---|---|---|
| rLP4-A35E, A37E | 0[b] | 0 |
| rLP4-A35N, A37N | 0 | 0 |
| rLP4-A35Q, A37Q | 0 | 0 |
| rLP4-A35T, A37T | 0 | 0 |
| rLP4-D184A, D185A | 0 | 0 |
| rLP4-D64A, D66A | 0 | 0 |
| rLP4-N218Q | 0.07 | 0.1 |
| rLP4-K161R | 0.26 | 0.4 |
| rLP4-wild-type | 70 | 100 |
| rLP4-D64E | 0.05 | 0.07 |
| rLP4-D64N | 0.13 | 0.2 |
| rLP4-Y122F | 66 | 94 |
| rLP4-Q39E | 2.3 | 3.3 |
| rLP4-F48C | ND[c] | ND |
| rLP4-F48S | 0.05 | 0.07 |

[a] Percentage of activity compared to wild-type rLP4.
[b] Below limit of detection.
[c] No data.

Every change made in the specific residues of P4 selected for conservation among bacterial acid phosphatases almost completely ablated the enzymatic activity of the P4 with the exception of the Y122F mutation. Of the remaining mutants tested, only the Q39E mutant retains >1% of wild-type activity (3.3%), while the double mutants have no detectable activity.

These results indicate that charge and tertiary structure within the areas of P4 conserved among bacterial acid phosphatases are critical to enzymatic function. Even conservative changes such as changing Asp residues to Glu residues, almost completely eliminated enzymatic activity when the changes were made at the conserved Asp residues.

With the exception of the Y122F and Q39E mutants, the inventors did not detect mutants with only partially reduced enzymatic activity. Virtually all of the mutations almost completely removed the activity. The mutation changing F48 to a cysteine or serine residue also reduced enzymatic activity.

Example 5

Production of Antisera Against Lipidated RLP4 Mutant Proteins

The mutant P4 proteins were then assayed for reactivity with monoclonal antibodies (Mabs) and the ability to elicit high titered, biologically active antisera against wild-type P4.

A. Immunization Procedures

Female Swiss Webster mice (6-8 weeks old) were subcutaneously immunized with 15 μg wild-type or mutant P4 protein mixed with 100 μg MPL™ adjuvant in saline or PBS. The composition also contained 0.01% thimerosal as a preservative. The two immunizations were performed four weeks apart, and the last bleed conducted at week six. The week zero and week six sera were analyzed individually or as pools by an ELISA assay and as pools for bactericidal activity.

B. Enzyme-linked Immunosorbent Assay (ELISA).

Anti-P4 (wild-type and mutant) antibodies were measured as follows. Plates were coated with 1 μg/ml wild-type P4 or 12 μg/ml mutant P4, diluted in PBS. After a 90 minute/37° C. incubation, the plates were stored at 4° C. until the next day. The mutant P4 coated plates were blocked with skim milk. After washing, a 100-μl aliquot of sera, serially diluted to a final concentration of from 1:50 to 1:5,467,500 in PBS/0.05% Tween 20, was added to each well and was incubated for 2 hours at room temperature. Plates were washed and 100 μl of secondary antibody (alkaline phosphatase conjugated goat anti-mouse IgG, diluted at 1:5,000 in PBS/0.05% Tween 20) was added and incubated for 2 hours at room temperature.

After washing, bound antibody was detected by the substrate pNPP (p-nitrophenol phosphate) diluted in diethanolamine at 1 mg/mi. After one hour, the yellow color was read at 405 nm with a 650 nm reference. Each reaction was carried out in duplicate, and the results were averaged. The anti-P4 titer of a serum was calculated as the dilution of the sera giving an absorbance of 0.1 on a 4-parameter curve.

C. Whole Cell ELISA

NTHi strain P860295 was grown on chocolate agar plates for six hours and harvested into PBS. The cell suspension was diluted to an O.D. of 0.2 determined at 620 nm and 75 μwas dispensed into NUNC polysorb plates. Plates were dried at 37° C. overnight and kept at room temperature until use. They were blocked with PBS/5% skim milk and washed prior to the addition of 100 μl diluted sera (serially diluted to a final concentration of either 1: 36,450 or 1,093,500 in PBS/0.1% Tween 20/5% skim milk). After a one hour/37° C. incubation, plates were washed and incubated another hour at 37° C. with 100 μl of secondary antibody (alkaline phosphatase conjugated goat anti-mouse IgG, diluted at 1:5,000 in PBS/0.1% Tween 20/5% skim milk).

Plates were washed again and bound antibodies were detected by the substrate pNPP (p-nitrophenol phosphate) diluted in diethanolamine at 1 mg/ml. After one hour, the yellow color was read at 405 nm with 650 nm reference. Each reaction was carried out in duplicate, and the results were averaged. The anti-whole cell titer of a serum was calculated as the dilution of the sera giving an absorbance of 0.1 on a 4-parameter curve.

Table 4 illustrates the results of the ELISA for the non-enzymatically active P4 mutants: P4-D184A, D185A and P4-D64A, D66A, which contained non-conservative mutations. The ELISA data demonstrated that these sites were involved in enzymatic activity and were important for immune response. Antibodies made against these mutant proteins showed that the mutant P4 proteins elicited significantly lower antibody titers against wild-type rLP4 than did either native P4 or wild-type rLP4.

TABLE 4

GMT ELISA Titers of Sera Directed Against Initial P4 Mutants.

| Immunogen | Protein Dose (μg) | Adjuvant (μg MPL) | ELISA Titer vs. Wild-Type rLP4 | | |
|---|---|---|---|---|---|
| | | | Preimmune (Pool Data) | Post-1° | Post-2° |
| *Haemophilus* P4 | 5 | 25 | 82 | 175,211 | 1,459,564 |
| rLP4 wild-type | 5 | 25 | 65 | 67,077 | 988,942 |
| rLP4-D184A, D185A | 5 | 25 | <50 | 2,684 | 139,033 |
| rLP4-D64A, D66A | 5 | 25 | <50 | 261 | 46,916 |

Table 5 reports the ELISA assay results for the P4 mutant proteins: (A35G, A37G), (A35T, A37T), (A35D, A37D), or (A35Q, A37Q). As stated above, the mutated genes encoding these proteins were inserted into the arabinose expression vector used for rLP4 (pBAD18cam), expressed in *E. coli* BLR, purified and used to immunize mice. Mice were immunized with 5 μg of appropriate P4 protein + MPL at weeks 0 and 4. Animals were bled at week 6. The data in Table 5 are from pools of 5 mice at the week 6 bleed. ELISA antibody titers against each of the homologous mutant P4 proteins and wild-type P4 were determined for each antiserum. In the table, ND means no data.

Each of the mutant proteins elicited good levels of antibodies directed against itself (the homologous protein). None of the proteins elicited comparable levels of antibodies against the wild-type rLP4. These results discount the possibility that the mutant P4 proteins are not good immunogens. Their titers against the homologous protein are within the normal range expected for a lipidated P4 in this model.

D. Bactericidal Assays.

The Bactericidal Antibody Assay is a functional measure for antibodies against NTHi and was performed as previously described by Green et al. 1991, cited above. Briefly, NTHi strain P860295 was grown at 37° C. overnight in BHI-XV broth. The overnight culture was diluted to an optical density of 30 Kletts in BHI-XV broth, as measured in a Klett-Sumerson photometer at 660 nm. The culture was incubated at 37° C. until mid-log phase and diluted 1:15,000 into PCM (approximately 1-2×10 cfu/mL). Anti-P4 mouse sera were heated at 55° C. for 30 minutes to remove complement activity. These sera were then serially diluted in phosphate-buffered saline containing 0.15 mM $CaCl_2$ and 0.5 mM $MgCl_2$ (PCM).

Human complement provided by the University of Rochester was adsorbed against NTHi P860295 (Green, B. A. et al, 1990 Infect. Immun., 58:3272-3278). In a 96-well microliter plate, 30 μl PCM, 5 μl diluted mouse antisera, 10 μl diluted NTHi, and 5 μl adsorbed human complement were combined

TABLE 5

ELISA response to rLP4 mutants mice versus rLP4 mutant proteins.

| Tested vs. | ELISA Titer of Anti- | | | | | | |
|---|---|---|---|---|---|---|---|
| | rLP4 | rLP4-D184A, D185A | rLP4-D64A, D66A | rLP4-A35N, A37N | rLp4-A35T, A37T | rLP4-A35Q, A37Q | rLP4-A35E, A37E |
| rLP4 | 300,956 | 172,866 | 113,618 | 6,877 | 9,582 | 11,432 | 20,955 |
| rLP4-D184A, D185A | 3,838 | 45,909 | ND | ND | ND | ND | ND |
| rLP4-D64A, D66A | 135 | ND | 256 | ND | ND | ND | ND |
| rLP4-A35N, A37N | 7,190 | ND | ND | 208,373 | ND | ND | ND |
| rLP4-A35T, A37T | 25,758 | ND | ND | ND | 74,934 | ND | ND |
| rLP4-A35Q, A37Q | 9,783 | ND | ND | ND | ND | 102,213 | 23,451 |
| rLP4-A35E, A37E | 23,589 | ND | ND | ND | ND | ND | 425,840 | and incubated at 37° C. for 30 minutes. The reactions were stopped by the addition of 200 μl PCM. Fifty μl from each well was plated on BHI-XV agar in duplicate and incubated overnight at 37° C. Colonies were counted to determine bactericidal titers (the reciprocal of the highest dilution of antiserum capable of killing at least 50% of bacteria compared with assay controls not containing antibodies).

Table 6 demonstrates the BC titers of the antisera made against P4-D184A, D185A and P4-D64A, D66A. These titers were determined and shown to be equivalent to those elicited by rLP4, within the error of the assay (Table 6 below). There was no correlation between BC titers and ELISA titers for these mutants.

TABLE 6

Bactericidal Activity of Antisera Vs. Mutants & Wild-Type P4

| Sera[a] | Bleed | BC Titer vs. NTHi P860295 |
| --- | --- | --- |
| Anti-native P4 | Post-2° | 160 |
| Anti- wild-type rLP4 | Post-2° | >320 |
| Anti-rLP4-D184A, D185A | Post-2° | 80 |
| Anti-rLP4-D64A, D66A | Post-2° | >320 |
| Preimmune pool | Preimmune | <20 |
| Anti-P860295 Whole Cell | Post-3° | >320 |
| Preimmune Pool | Preimmune | <20 |

[a]Pools of sera from 10 mice.

Table 7 reports the BC assay results for sera of mice immunized with the double mutant proteins: (A35G, A37G), (A35T, A37T), (A35D, A37D), or (A35Q, A37Q). The bactericidal antibody titers did not correlate with the ELISA titers against wild-type P4. For example, the rLP4 A35N, A37N mutant did not elicit high ELISA titers against wild-type rLP4, but did elicit good bactericidal antibody titers against NTHi. Thus, none of these mutants were considered to be good immunogenic or vaccine components. Interestingly, the anti-rLP4 serum did not react very strongly against the majority of the mutants, which seems to indicate that the enzymatically active site is also immunodominant.

TABLE 7

ELISA and BC Titers of Anti-rLP4 and Anti-P4 Mutant Sera

| Immunogen | ELISA vs wild-type rLP4 | | | BC titer vs. P860295 | |
| --- | --- | --- | --- | --- | --- |
| | Wk 0 | Wk 4 | Wk 6 | Assay 1 | Assay 2 |
| rLP4 F48C, 15 μg | <50 | 168,444 | 926,370 | 320 | 320 |
| rLP4, 15 μg | <50 | 447,596 | 670,310 | 160 | 160 |
| rLP4 N218Q, 15 μg | <50 | 217,526 | 1,730,005 | 320 | 80 |
| rLP4 K161R, 15 μg | 53 | 393,031 | 359,835 | 80 | 40 |
| rLP4-D184A, D185A, 15 μg | <50 | 81,847 | 83,045 | 40 | 20 |
| rLP4-D64A, D66A 15 μg | <50 | 181,109 | 249,068 | 20 | 40 |
| rLP4-A35N, A37N, 15 μg | <50 | 16,903 | 14,597 | 320 | 80 |
| rLP4-A35Q, A37Q 15 μg | <50 | 38,697 | 63,864 | <20 | 80 |
| rLP4-A35E, A37E 15 μg | <50 | 23,817 | 25,041 | <20 | 40 |
| Pre-immune mouse serum | ND | ND | ND | <20 | <20 |
| rLP4, 5 μg (positive control) | ND | ND | | 160 | |

Table 8 reports the results of the BC assay for the lipidated proteins with the single mutations: N218Q, K161R, D64E, Y122F, D64N, D64E, F48C, and Q39E, which were purified from *E. coli* BLR cells, and examined for enzymatic activity. When the proteins were used to immunize mice, three mutants seemed to have a combination of high ELISA titers and high BC titers, along with no detectable enzymatic activity. These were the F48C, N218Q, and Q39E mutations (Tables 7 and 8). These mutant P4 proteins had ELISA titers against wild-type P4 equivalent to wild-type P4, but also had high bactericidal titers against NTHi.

TABLE 8

ELISA and BC Titers of Mutant P4 Proteins

| Mutant | IgG titer | BC Titer vs. P860295 |
| --- | --- | --- |
| rLP4-D64N | 1,921,553* | 20 |
| rLP4-N218Q | 1,475,833** | 200 |
| rLP4Y122F | 1,106,822* | 40 |
| rLP4D64E | 988,016* | 20 |
| rLP4-Q39E | 770,483* | 320 |
| rLP4-F48C | 687,742** | 240 |
| rLP4 | 197,160** | 160 |
| rLP4-K161R | 186,394** | 60 |
| rLP4-D64A, D66A | 60,358** | 30 |
| rLP4-D184A, D185A | 33,185** | 30 |
| rLP4-A35Q, A37Q | 14,331** | 50 |
| rLP4- A35N, A37N | 7,121** | 200 |
| rLP4- A35E, A37E | 4,322** | 30 |

*from pooled sera of 10 mice
**GMT from individual sera of 10 mice

Example 6

P4 Truncation Mutants

Four P4 variant proteins truncated at various points at the C-terminus of the wild-type sequence were constructed. Truncation mutants were generated by PCR of the hel gene in pLP339. Briefly, a primer homologous to the 5' prime end of the hel gene and ribosome binding site was synthesized with a SphI site at its 5' end. 3' primers were synthesized that changed the residue after the designated truncation point to a stop codon, but were homologous to the hel gene at the primers' 3' ends. The 5' end of the second primer also contained a SacI site. PCR products were cloned into pCR2.1-TOPO (Invitrogen) and digested with SphI-SacI. The hel gene fragments were purified and ligated into pBAD18Cam digested with the same enzymes. Positive clones were identified and tested for expression. All of the constructs expressed truncated P4 proteins that were lipidated in *E. coli* BLR.

Specifically, P4 variant proteins truncated at residue 200 (that is, it contains amino acids 1-200 of SEQ ID NO:3), 210, 221 and 232 were generated. Each fragment was assayed for phosphatase activity using the protocol set forth in Example 4. All four fragments had no detectable enzyme activity.

Next, Swiss Webster mice were immunized following the protocol of Example 5A, except that 5 μg of truncated P4 protein mixed with 25 μg of MPL™ were administered. Table 9 illustrates the results of an ELISA for the four truncated P4 fragments compared with wild-type rLP4, where the protocol of Example 5 was followed. The legend "rLP4-232" indicates that the recombinant P4 was truncated at amino acid 232 of SEQ ID NO:3, and so forth. The ELISA data demonstrated that all four truncation mutants elicited useful titer levels.

TABLE 9

Anti-rP4 ELISA Titers of P4 Truncation
Mutants in Swiss Webster Mice

| Immunogen | Week 0 | Week 4 | Week 6 |
|---|---|---|---|
| rLP4/MPL™ | 53 | 155,797 | 1,477,755 |
| RLP4-232/MPL™ | <50 | 31,611 | 664.876 |
| RLP4-221/MPL™ | 53 | 31,032 | 506,025 |
| RLP4-210/MPL™ | <50 | 66,125 | 888,795 |
| RLP4-200/MPL™ | 62 | 11,936 | 631,073 |

Next, two bactericidal assays were conducted following the protocol of Example 5D. In the first assay, the P4 protein truncated at amino acid 210 was compared to wild-type rLP4 and various P4 variants described above, where each formulation included 15 μg of P4 protein mixed with 100 μg of MPL™, except for the last group, in which only 5 μg of rLP4 protein from a prior study was included as a positive control. The bactericidal assay data in Table 10 indicated that the P4 protein truncated at amino acid 210 elicited bactericidal antibody titers that were statistically significant from background. In this experiment, $BC_{50}$ titers of 80 or higher were considered to be significantly different from background (<20). The Complement used was adsorbed human UR8-96.

TABLE 10

Bactericidal Activity of Antisera vs.
Mutants, Truncation & Wild-Type P4

| | | P860295 | |
|---|---|---|---|
| Mouse Sera | Description | Assay 1 | Assay 2 |
| AG581 wk6 | rLP4 F48C | 320 | 320 |
| AG582 wk6 | rLP4 | 160 | 160 |
| AG583 wk6 | rLP4 N218Q | 320 | 80 |
| AG584 wk6 | rLP4 K161R | 80 | 40 |
| AG585 wk6 | rLP4 D184A, D185A | 40 | 20 |
| AG586 wk6 | rLP4 D64A, D66A | 20 | 40 |
| AG587 wk6 | rLP4 A35N, A37N | 320 | 80 |
| AG588 wk6 | rLP4-210 | 80 | 80 |
| AG589 wk6 | rLP4 A35Q, A37Q | <20 | 80 |
| AG590 wk6 | rLP4 A35E, A37E | <20 | 40 |
| wk 0 pool | pre-immune mouse serum (negative control) | <20 | <20 |
| AC443 wk6 | rLP4 (positive control) | | 160 |

In the second assay, the P4 proteins truncated at amino acids 200, 210, 221 and 232 were compared to wild-type rLP4 and various P4 variants described above, where each formulation included 5 μg of P4 protein mixed with 25 μg of MPL™ (a suboptimal amount), except for the last group, in which 5 μg of rLP4 protein plus 100 μg of MPL™ from a prior study was included as a positive control. The bactericidal assay data in Table 11 indicated that the P4 protein truncated at amino acids 221 and 232 elicited bactericidal antibody titers that were statistically significant from background, even with the low dose of MPL™. In this experiment, the $BC_{50}$ titers of 80 or higher were considered to be significantly different than week 0. The Complement used was adsorbed human UR8-97.

TABLE 11

Bactericidal Activity of Antisera vs.
Mutants, Truncations & Wild-Type P4

| Mouse serum | Description | P860295 |
|---|---|---|
| AF208 wk6 | rLP4 | <20 |
| AF209 wk6 | rLP4 D184A, D185A | 80 |
| AF210 wk6 | rLP4 D64A, D66A | <20 |
| AF211 wk6 | rLP4 A35N, A37N | <20 |
| AF212 wk6 | rLP4 A35T, A37T | 20 |
| AF213 wk6 | rLP4 A35Q, A37Q | 40 |
| AF214 wk6 | rLP4 A35E, A37E | 40 |
| AF215 wk6 | rLP4 | <20 |
| AF216 wk6 | rLP4-232 | 80 |
| AF217 wk6 | rLP4-221 | 80 |
| AF218 wk6 | rLP4-210 | 40 |
| AF219 wk6 | rLP4-200 | <20 |
| wk 0 pool | Pre-immune mouse serum (negative control) | <20 |
| AC443 wk6 | rPL4 (positive control) | 160 |

In summary, the results of the proposed P4 mutations indicate that the separation of ELISA titer from bactericidal activity may mean that the sites required for bactericidal activity are distinct from areas essential for enzymatic activity.

All publications cited in this specification are incorporated herin by reference. While the invention has been described with reference to a particularly preferred embodiment, it will be appreciated that modifications can be made without departing from the spirit of the invention. Such modifications are intended to fall within the scope of the appended claims.

The invention claimed is:

1. An isolated P4 variant protein of non-typable *Haemophilus influenzae* (NTHi) that has reduced phosphatase activity compared to wild-type P4 protein and that induces antibody to wild-type P4 protein, said antibody having bactericidal activity against NTHi, wherein the P4 variant protein has a mutation selected from the group consisting of:

(a) a mutation at amino acid residue 39 of SEQ ID NO:3, which is a glutamine in wild-type P4 protein;

(b) a mutation at amino acid residue 48 of SEQ ID NO:3, which is a phenylalanine in wild-type P4 protein;

(c) a mutation at amino acid residue 64 of SEQ ID NO:3, which is an aspartic acid in wild-type P4 protein;

(d) a mutation at amino acid residue 161 of SEQ ID NO:3, which is a lysine in wild-type P4 protein;

(e) a mutation at amino acid residue 218 of SEQ ID NO:3, which is an asparagine in wild-type P4 protein;

(f) mutations at amino acid residues 35 and 37 of SEQ ID NO:3, which are alanine in wild-type P4 protein, where the mutations are not glutamic acid, glutamine or threonine;

(g) mutations at amino acid residues 64 and 66 of SEQ ID NO:3, which are aspartic acid in wild-type P4 protein; and (h) combinations of one or more of the mutations of (a)-(g).

2. An isolated P4 variant protein of non-typable *Haemophilus influenzae* (NTHi) that has reduced phosphatase activity compared to wild-type P4 protein and that induces antibody to wild-type P4 protein, said antibody having bactericidal activity against NTHi, wherein the P4 variant protein has a mutation selected from the group consisting of:

(a) a glutamic acid, aspartic acid or asparagine in place of glutamine at wild-type amino acid residue 39 of SEQ ID NO:3;

(b) a cysteine, serine or other amino acids which have uncharged polar groups in place of phenylalanine at wild-type amino acid residue 48 of SEQ ID NO:3;

(c) an asparagine, glutamic acid or alanine in place of aspartic acid at wild-type amino acid residue 64 of SEQ ID NO:3;

(d) an arginine in place of lysine at wild-type amino acid residue 161 of SEQ ID NO:3;

(e) a glutamine, aspartic acid or glutamic acid in place of asparagine at wild-type amino acid residue 218 of SEQ ID NO:3;

(f) an asparagine in place of alanine at wild-type amino acid residues 35 and 37 of SEQ ID NO:3;

(g) an alanine, asparagine or glutamic acid in place of aspartic acid at wild-type amino acid residues 64 and 66 of SEQ ID NO:3; and (h) combinations of one or more of the mutations of (a)-(g).

3. The P4 variant protein according to claim 2, wherein said variant protein is lipidated.

4. The P4 variant protein according to claim 3, further comprising a signal peptide fused to the N-terminus of said P4 variant protein.

5. The P4 variant protein according to claim 4, wherein said signal peptide is amino acids 1-20 of SEQ ID NO:2.

6. The P4 variant protein according to claim 2, wherein said variant protein is non-lipidated.

7. The P4 variant protein according to claim 2, wherein said variant protein is fused in frame with a carrier protein.

8. The P4 variant protein according to claim 7, wherein said carrier protein is selected from the group consisting of an *E. coli* DnaK protein, a GST protein, a mycobacterial heat shock protein 70, a diphtheria toxoid, a tetanus toxoid, a galactokinase, an ubiquitin, an α-mating factor, a β-galactosidase, and an influenza NS-1 protein.

9. An immunogenic composition comprising the P4 variant protein according to claim 1 and a pharmaceutically acceptable carrier.

10. The immunogenic composition according to claim 9, further comprising an adjuvant.

11. The immunogenic composition according to claim 9, further comprising an additional antigen from *H. influenzae* or a microorganism other than *H. influenzae*.

12. An immunogenic composition comprising the P4 variant protein according to claim 2 and a pharmaceutically acceptable carrier.

13. The immunogenic composition according to claim 12, further comprising an adjuvant.

14. The immunogenic composition according to claim 12, further comprising an additional antigen from *H. influenzae* or a microorganism other than *H. influenzae*.

15. An isolated P4 variant protein of non-typable *Haemophilus influenzae* (NTHi) that has reduced phosphatase activity compared to wild-type P4 protein and that induces antibody to wild-type P4 protein, said antibody having bactericidal activity against NTHi, wherein the P4 variant protein consists of amino acids at positions 1-200, 1-210, 1-221 or 1-232 of SEQ ID NO: 3.

16. The P4 variant protein according to claim 15, which further comprises one or more mutations selected from the group consisting of:

(a) a mutation at amino acid residue 39 of SEQ ID NO:3, which is a glutamine in wild-type P4 protein;

(b) a mutation at amino acid residue 48 of SEQ ID NO:3, which is a phenylalanine in wild-type P4 protein;

(c) a mutation at amino acid residue 64 of SEQ ID NO:3, which is an aspartic acid in wild-type P4 protein;

(d) a mutation at amino acid residue 161 of SEQ ID NO:3, which is a lysine in wild-type P4 protein;

(e) mutations at amino acid residues 35 and 37 of SEQ ID NO:3, which are alanine in wild-type P4 protein, where the mutations are not glutamic acid, glutamine or threonine;

(f) mutations at amino acid residues 64 and 66 of SEQ ID NO:3, which are aspartic acid in wild-type P4 protein; and (g) combinations of one or more of the mutations of (a)-(f).

17. The P4 variant protein according to claim 15, wherein the P4 variant protein has a mutation selected from the group consisting of:

(a) a glutamic acid, aspartic acid or asparagine in place of glutamine at wild-type amino acid residue 39 of SEQ ID NO:3;

(b) a cysteine, serine or other amino acids which have uncharged polar groups in place of phenylalanine at wild-type amino acid residue 48 of SEQ ID NO:3;

(c) an asparagine, glutamic acid or alanine in place of aspartic acid at wild-type amino acid residue 64 of SEQ ID NO:3;

(d) an arginine in place of lysine at wild-type amino acid residue 161 of SEQ ID NO:3;

(e) an asparagine in place of alanine at wild-type amino acid residues 35 and 37 of SEQ ID NO:3;

(f) an alanine, asparagine or glutamic acid in place of aspartic acid at wild-type amino acid residues 64 and 66 of SEQ ID NO:3; and (g) combinations of one or more of the mutations of (a)-(f).

18. An immunogenic composition comprising the P4 variant protein according to claim 15 and a pharmaceutically acceptable carrier.

19. The immunogenic composition according to claim 18, further comprising an adjuvant.

20. The immunogenic composition according to claim 18, further comprising an additional antigen from *H. influenzae* or a microorganism other than *H. influenzae*.

21. An immunogenic composition comprising the P4 variant protein according to claim 17 and a pharmaceutically acceptable carrier.

22. The immunogenic composition according to claim 21, further comprising an adjuvant.

23. The immunogenic composition according to claim 21, further comprising an additional antigen from *H. influenzae* or a microorganism other than *H. influenzae*.

24. A method for inducing an immune response in a human against non-typable *H. influenzae* comprising the steps of: administering to said human an effective amount of the immunogenic composition of claim 9.

25. A method for inducing an immune response in a human against non-typable *H. influenzae* comprising the steps of:
    administering to said human an effective amount of the immunogenic composition of claim 18.

26. The P4 variant protein according to claim 2, which serves as a carrier protein for another antigen.

27. The P4 variant protein according to claim 26, which is chemically conjugated to a polysaccharide, oligosaccharide, saccharide, lipopolysaccharide, lipooligosaccharide or liposaccharide.

28. The P4 variant protein according to claim 26, which is fused to a protein, polypeptide or peptide.

29. The P4 variant protein according to claim 15, which serves as a carrier protein for another antigen.

30. The P4 variant protein according to claim 29, which is chemically conjugated to a polysaccharide, oligosaccharide, saccharide, lipopolysaccharide, lipooligosaccharide or liposaccharide.

31. The P4 variant protein according to claim 29, which is fused to a protein, polypeptide or peptide.

32. An isolated P4 variant protein of non-typable *Haemophilus influenzae* (NTHi) that has reduced phosphatase activity compared to wild-type P4 protein and that induces antibody to wild-type P4 protein, said antibody having bactericidal activity against NTHi, wherein the P4 variant protein consists of amino acids at positions 1-221 or 1-232 of SEQ ID NO: 3, further comprising a mutation at amino acid residue 218 of SEQ ID NO:3, which is an asparagine in wild-type P4 protein.

33. An isolated P4 variant protein of non-typable *Haemophilus influenzae* (NTHi) that has reduced phosphatase activity compared to wild-type P4 protein and that induces antibody to wild-type P4 protein, said antibody having bactericidal activity against NTHi, wherein the P4 variant protein consists of amino acids at positions 1-221 or 1-232 of SEQ ID NO:3, and has a glutamine, aspartic acid or glutamic acid at amino acid residue 218 of SEQ ID NO:3.

34. A method for inducing an immune response in a human against non-typable *H. influenzae* comprising the steps of:
    administering to said human an effective amount of the immunogenic composition of claim 12.

* * * * *

UNITED STATES PATENT AND TRADEMARK OFFICE
CERTIFICATE OF CORRECTION

PATENT NO. : 7,615,229 B2  
APPLICATION NO. : 10/507786  
DATED : November 10, 2009  
INVENTOR(S) : Green et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 958 days.

Signed and Sealed this

Nineteenth Day of October, 2010

David J. Kappos  
*Director of the United States Patent and Trademark Office*

SEQUENCE LISTING

```
<160> NUMBER OF SEQ ID NOS: 29

<210> SEQ ID NO 1
<211> LENGTH: 1143
<212> TYPE: DNA
<213> ORGANISM: hel gene of a bacterium H. influenzae

<400> SEQUENCE: 1
gaattcttaa aaggaataaa ataatttcta ttataaccgt aggtagttta tttacggtta    60
ttaatgccat ctatgatgaa aaacactttt caattgaaaa gtgttttttca gaaagactta   120 ctataccctg aatgaatagg aacataatat gaaaacaacg ttaaaaatga ccgcacttgc   180 ggctcttttct gcttttgttt tagctggctg tggttcacac caaatgaaat cagaagaaca   240
```

-continued

```
tgcaaatatg caattacaac aacaagcggt gcttggatta aactggatgc aagattctgg    300
cgaatataaa gcattagctt atcaagcgta caatgcggca aaagttgcat ttgatcacgc    360
aaaagtggca aaggtaaga aaaaagcggt tgtggctgat ttagatgaaa ctatgttaga    420
caacagccct tatgctggct ggcaagttca aaataacaaa ccattcgatg gtaaagattg    480
gactcgttgg gtagacgcac gtcaatctcg tgccgttccg ggtgcggtag aatttaataa    540
ttatgtaaac agccacaacg gtaaagtgtt ctacgtaaca aaccgcaaag acagcactga    600
aaaatcaggc actatcgatg atatgaaacg cttaggtttc aatggcgtgg aagaatctgc    660
attttatttg aaaaaagaca atcagctaa agcggctcgt tttgcagaaa ttgaaaaaca    720
aggctatgaa atcgtacttt atgtaggtga taacttagat gacttcggta ataccgtata    780
tggcaaatta aacgctgacc gccgtgcatt cgttgatcaa aaccaaggca aatttggtaa    840
aactttcatc atgttaccta acgcaaacta cggtggctgg gaaggcggtt tagctgaagg    900
gtatttcaaa aaagatacac aaggccaaat caaagctcgt ttagatgcag tacaagcttg    960
ggatggtaaa taattttcca ttaaaaagat cgatttaaat atcgattttg aaaatttaat   1020 tgagggcta agctcagttt ttactggctt agcttttca ttttcagtca ctcaagtatc    1080
atcattacta catctgagtt tgctatgatg ttgcagcttc aaatgatcaa gtagagaatg   1140
acc                                                                 1143
```

<210> SEQ ID NO 2
<211> LENGTH: 274
<212> TYPE: PRT
<213> ORGANISM: hel gene of a bacterium H. influenzae

<400> SEQUENCE: 2

```
Met Lys Thr Thr Leu Lys Met Thr Ala Leu Ala Ala Leu Ser Ala Phe
 1               5                  10                  15

Val Leu Ala Gly Cys Gly Ser His Gln Met Lys Ser Glu Glu His Ala
             20                  25                  30

Asn Met Gln Leu Gln Gln Gln Ala Val Leu Gly Leu Asn Trp Met Gln
         35                  40                  45

Asp Ser Gly Glu Tyr Lys Ala Leu Ala Tyr Gln Ala Tyr Asn Ala Ala
     50                  55                  60

Lys Val Ala Phe Asp His Ala Lys Val Ala Lys Gly Lys Lys Lys Ala
 65                  70                  75                  80

Val Val Ala Asp Leu Asp Glu Thr Met Leu Asp Asn Ser Pro Tyr Ala
                 85                  90                  95

Gly Trp Gln Val Gln Asn Asn Lys Pro Phe Asp Gly Lys Asp Trp Thr
            100                 105                 110

Arg Trp Val Asp Ala Arg Gln Ser Arg Ala Val Pro Gly Ala Val Glu
        115                 120                 125

Phe Asn Asn Tyr Val Asn Ser His Asn Gly Lys Val Phe Tyr Val Thr
    130                 135                 140

Asn Arg Lys Asp Ser Thr Glu Lys Ser Gly Thr Ile Asp Asp Met Lys
145                 150                 155                 160

Arg Leu Gly Phe Asn Gly Val Glu Glu Ser Ala Phe Tyr Leu Lys Lys
                165                 170                 175

Asp Lys Ser Ala Lys Ala Ala Arg Phe Ala Glu Ile Glu Lys Gln Gly
            180                 185                 190

Tyr Glu Ile Val Leu Tyr Val Gly Asp Asn Leu Asp Asp Phe Gly Asn
        195                 200                 205
```

```
Thr Val Tyr Gly Lys Leu Asn Ala Asp Arg Arg Ala Phe Val Asp Gln
    210                 215                 220

Asn Gln Gly Lys Phe Gly Lys Thr Phe Ile Met Leu Pro Asn Ala Asn
225                 230                 235                 240

Tyr Gly Gly Trp Glu Gly Gly Leu Ala Glu Gly Tyr Phe Lys Lys Asp
                    245                 250                 255

Thr Gln Gly Gln Ile Lys Ala Arg Leu Asp Ala Val Gln Ala Trp Asp
            260                 265                 270

Gly Lys

<210> SEQ ID NO 3
<211> LENGTH: 254
<212> TYPE: PRT
<213> ORGANISM: hel gene of a bacterium H. influenzae

<400> SEQUENCE: 3

Cys Gly Ser His Gln Met Lys Ser Glu Glu His Ala Asn Met Gln Leu
1               5                   10                  15

Gln Gln Gln Ala Val Leu Gly Leu Asn Trp Met Gln Asp Ser Gly Glu
            20                  25                  30

Tyr Lys Ala Leu Ala Tyr Gln Ala Tyr Asn Ala Ala Lys Val Ala Phe
        35                  40                  45

Asp His Ala Lys Val Ala Lys Gly Lys Lys Ala Val Val Ala Asp
    50                  55                  60

Leu Asp Glu Thr Met Leu Asp Asn Ser Pro Tyr Ala Gly Trp Gln Val
65                  70                  75                  80

Gln Asn Asn Lys Pro Phe Asp Gly Lys Asp Trp Thr Arg Trp Val Asp
                85                  90                  95

Ala Arg Gln Ser Arg Ala Val Pro Gly Ala Val Glu Phe Asn Asn Tyr
            100                 105                 110

Val Asn Ser His Asn Gly Lys Val Phe Tyr Val Thr Asn Arg Lys Asp
        115                 120                 125

Ser Thr Glu Lys Ser Gly Thr Ile Asp Asp Met Lys Arg Leu Gly Phe
    130                 135                 140

Asn Gly Val Glu Glu Ser Ala Phe Tyr Leu Lys Lys Asp Lys Ser Ala
145                 150                 155                 160

Lys Ala Ala Arg Phe Ala Glu Ile Glu Lys Gln Gly Tyr Glu Ile Val
                165                 170                 175

Leu Tyr Val Gly Asp Asn Leu Asp Asp Phe Gly Asn Thr Val Tyr Gly
            180                 185                 190

Lys Leu Asn Ala Asp Arg Arg Ala Phe Val Asp Gln Asn Gln Gly Lys
        195                 200                 205

Phe Gly Lys Thr Phe Ile Met Leu Pro Asn Ala Asn Tyr Gly Gly Trp
    210                 215                 220

Glu Gly Gly Leu Ala Glu Gly Tyr Phe Lys Lys Asp Thr Gln Gly Gln
225                 230                 235                 240

Ile Lys Ala Arg Leu Asp Ala Val Gln Ala Trp Asp Gly Lys
                245                 250

<210> SEQ ID NO 4
<211> LENGTH: 28
<212> TYPE: DNA
<213> ORGANISM: artificial sequence
<220> FEATURE:
<223> OTHER INFORMATION: synthetic oligonucleotide primer
```

```
<400> SEQUENCE: 4
gcaaaagttg catgcgatca cgcaaaag                                    28

<210> SEQ ID NO 5
<211> LENGTH: 28
<212> TYPE: DNA
<213> ORGANISM: artificial sequence
<220> FEATURE:
<223> OTHER INFORMATION: synthetic oligonucleotide primer

<400> SEQUENCE: 5
cttttgcgtg atcgcatgca acttttgc                                    28

<210> SEQ ID NO 6
<211> LENGTH: 34
<212> TYPE: DNA
<213> ORGANISM: artificial sequence
<220> FEATURE:
<223> OTHER INFORMATION: synthetic oligonucleotide primer

<400> SEQUENCE: 6
gcggttgtgg ctgctttagc tgaaactatg ttag                             34

<210> SEQ ID NO 7
<211> LENGTH: 34
<212> TYPE: DNA
<213> ORGANISM: artificial sequence
<220> FEATURE:
<223> OTHER INFORMATION: synthetic oligonucleotide primer

<400> SEQUENCE: 7
ctaacatagt ttcagctaaa gcagccacaa ccgc                             34

<210> SEQ ID NO 8
<211> LENGTH: 51
<212> TYPE: DNA
<213> ORGANISM: artificial sequence
<220> FEATURE:
<223> OTHER INFORMATION: synthetic oligonucleotide primer

<400> SEQUENCE: 8
gcgcgtctct tgcattttat ttgaaaaaag acaaatcagc tagagcggct c           51

<210> SEQ ID NO 9
<211> LENGTH: 37
<212> TYPE: DNA
<213> ORGANISM: artificial sequence
<220> FEATURE:
<223> OTHER INFORMATION: synthetic oligonucleotide primer

<400> SEQUENCE: 9
gcgcgtctcg tgcagattct tccacgccat tgaaacc                          37

<210> SEQ ID NO 10
<211> LENGTH: 34
<212> TYPE: DNA
<213> ORGANISM: artificial sequence
<220> FEATURE:
<223> OTHER INFORMATION: synthetic oligonucleotide primer

<400> SEQUENCE: 10
gcgcgtctct gctgggaagg cggtttagct gaag                             34

<210> SEQ ID NO 11
<211> LENGTH: 47
```

```
<212> TYPE: DNA
<213> ORGANISM: artificial sequence
<220> FEATURE:
<223> OTHER INFORMATION: synthetic oligonucleotide primer

<400> SEQUENCE: 11
gcgcgtctcg cagccaccgt agtttgcttg aggtaacatg atgaaag        47

<210> SEQ ID NO 12
<211> LENGTH: 44
<212> TYPE: DNA
<213> ORGANISM: artificial sequence
<220> FEATURE:
<223> OTHER INFORMATION: synthetic oligonucleotide primer

<400> SEQUENCE: 12
gcgcgtctct ggtaagaaaa aagcggttgt ggctaattta gatg           44

<210> SEQ ID NO 13
<211> LENGTH: 32
<212> TYPE: DNA
<213> ORGANISM: artificial sequence
<220> FEATURE:
<223> OTHER INFORMATION: synthetic oligonucleotide primer

<400> SEQUENCE: 13
gcgcgtctcg tacctttgc cacttttgcg tg                         32

<210> SEQ ID NO 14
<211> LENGTH: 32
<212> TYPE: DNA
<213> ORGANISM: artificial sequence
<220> FEATURE:
<223> OTHER INFORMATION: synthetic oligonucleotide primer

<400> SEQUENCE: 14
gcgcgtctcg tacctttgc cacttttgcg tg                         32

<210> SEQ ID NO 15
<211> LENGTH: 44
<212> TYPE: DNA
<213> ORGANISM: artificial sequence
<220> FEATURE:
<223> OTHER INFORMATION: synthetic oligonucleotide primer

<400> SEQUENCE: 15
gcgcgtctct ggtaagaaaa aagcggttgt ggctgaatta gatg           44

<210> SEQ ID NO 16
<211> LENGTH: 36
<212> TYPE: DNA
<213> ORGANISM: artificial sequence
<220> FEATURE:
<223> OTHER INFORMATION: synthetic oligonucleotide primer

<400> SEQUENCE: 16
cgccgtctcg ctgccttcgg taataccgta tatggc                    36

<210> SEQ ID NO 17
<211> LENGTH: 40
<212> TYPE: DNA
<213> ORGANISM: artificial sequence
<220> FEATURE:
<223> OTHER INFORMATION: synthetic oligonucleotide primer

<400> SEQUENCE: 17
```

-continued cgccgtctcg gcagctaagt tatcacctac ataaagtacg        40

<210> SEQ ID NO 18
<211> LENGTH: 35
<212> TYPE: DNA
<213> ORGANISM: artificial sequence
<220> FEATURE:
<223> OTHER INFORMATION: synthetic oligonucleotide primer

<400> SEQUENCE: 18
cgccgtctct tagaatatca agcgtacaat gcggc             35

<210> SEQ ID NO 19
<211> LENGTH: 40
<212> TYPE: DNA
<213> ORGANISM: artificial sequence
<220> FEATURE:
<223> OTHER INFORMATION: synthetic oligonucleotide primer

<400> SEQUENCE: 19
ccgcgtctca tctaattctt tatattcgcc agaatcttgc        40

<210> SEQ ID NO 20
<211> LENGTH: 37
<212> TYPE: DNA
<213> ORGANISM: artificial sequence
<220> FEATURE:
<223> OTHER INFORMATION: synthetic oligonucleotide primer

<400> SEQUENCE: 20
gcccgtctcc cttaaactat caagcgtaca atgcggc           37

<210> SEQ ID NO 21
<211> LENGTH: 38
<212> TYPE: DNA
<213> ORGANISM: artificial sequence
<220> FEATURE:
<223> OTHER INFORMATION: synthetic oligonucleotide primer

<400> SEQUENCE: 21
gcccgtctcc taagtttta tattcgccag aatcttgc           38

<210> SEQ ID NO 22
<211> LENGTH: 36
<212> TYPE: DNA
<213> ORGANISM: artificial sequence
<220> FEATURE:
<223> OTHER INFORMATION: synthetic oligonucleotide primer

<400> SEQUENCE: 22
ccgcgtctca ttacaatatc aagcgtacaa tgcggc            36

<210> SEQ ID NO 23
<211> LENGTH: 39
<212> TYPE: DNA
<213> ORGANISM: artificial sequence
<220> FEATURE:
<223> OTHER INFORMATION: synthetic oligonucleotide primer

<400> SEQUENCE: 23
gcccgtctcg gtaattgttt atattcgcca gaatcttgc         39

<210> SEQ ID NO 24
<211> LENGTH: 37
<212> TYPE: DNA
<213> ORGANISM: artificial sequence

```
<220> FEATURE:
<223> OTHER INFORMATION: synthetic oligonucleotide primer

<400> SEQUENCE: 24
cggcgtctcc attaacttat caagcgtaca atgcggc                         37

<210> SEQ ID NO 25
<211> LENGTH: 38
<212> TYPE: DNA
<213> ORGANISM: artificial sequence
<220> FEATURE:
<223> OTHER INFORMATION: synthetic oligonucleotide primer

<400> SEQUENCE: 25
cggcgtctcc taatgtttta tattcgccag aatcttgc                        38

<210> SEQ ID NO 26
<211> LENGTH: 28
<212> TYPE: DNA
<213> ORGANISM: artificial sequence
<220> FEATURE:
<223> OTHER INFORMATION: synthetic oligonucleotide primer

<400> SEQUENCE: 26
gcattagctt atgaagcgta caatgcgg                                   28

<210> SEQ ID NO 27
<211> LENGTH: 28
<212> TYPE: DNA
<213> ORGANISM: artificial sequence
<220> FEATURE:
<223> OTHER INFORMATION: synthetic oligonucleotide primer

<400> SEQUENCE: 27
ccgcattgta cgcttcataa gctaatgc                                   28

<210> SEQ ID NO 28
<211> LENGTH: 28
<212> TYPE: DNA
<213> ORGANISM: artificial sequence
<220> FEATURE:
<223> OTHER INFORMATION: synthetic oligonucleotide primer

<400> SEQUENCE: 28
cggtaaagtg ttctttgtaa caaaccgc                                   28

<210> SEQ ID NO 29
<211> LENGTH: 28
<212> TYPE: DNA
<213> ORGANISM: artificial sequence
<220> FEATURE:
<223> OTHER INFORMATION: synthetic oligonucleotide primer

<400> SEQUENCE: 29
gcggtttgtt acaagaaca ctttaccg                                    28
```